US00RE49007E

(19) United States
(12) Reissued Patent
Al-Ali

(10) Patent Number: US RE49,007 E
(45) Date of Reissued Patent: *Apr. 5, 2022

(54) ADAPTIVE ALARM SYSTEM

(71) Applicant: MASIMO Corporation, Irvine, CA (US)

(72) Inventor: Ammar Al-Ali, San Juan Capistrano, CA (US)

(73) Assignee: MASIMO CORPORATION, Irvine, CA (US)

( * ) Notice: This patent is subject to a terminal disclaimer.

(21) Appl. No.: 16/800,971

(22) Filed: Feb. 25, 2020

Related U.S. Patent Documents

Reissue of:
(64) Patent No.: 9,775,570
Issued: Oct. 3, 2017
Appl. No.: 15/583,718
Filed: May 1, 2017

U.S. Applications:
(63) Continuation of application No. 16/184,908, filed on Nov. 8, 2018, now Pat. No. Re. 47,882, which is a (Continued)

(51) Int. Cl.
*A61B 5/00* (2006.01)
*A61B 5/1455* (2006.01)
*G08B 29/26* (2006.01)

(52) U.S. Cl.
CPC ..... *A61B 5/746* (2013.01); *A61B 5/1455* (2013.01); *A61B 5/14551* (2013.01); (Continued)

(58) Field of Classification Search
CPC ..... A61B 5/14551; A61B 5/1455
See application file for complete search history.

(56) References Cited

U.S. PATENT DOCUMENTS 3,608,545 A 9/1971 Novak et al.
4,338,950 A 7/1982 Barlow, Jr. et al.
(Continued)

FOREIGN PATENT DOCUMENTS

EP 0880936 A2 12/1998
EP 0920729 B1 4/2000
(Continued)

OTHER PUBLICATIONS

US 9,579,050 B2, 02/2017, Al-Ali (withdrawn)
(Continued)

*Primary Examiner* — Robert L Nasser
(74) *Attorney, Agent, or Firm* — Knobbe Martens Olson & Bear, LLP

(57) ABSTRACT

Systems and electronic processes for reducing electronic alarms in a medical patient monitoring system. For example, a system for reducing electronic alarms can include an optical sensor and one or more hardware processors in electronic communication with the optical sensor. The one or more hardware processors can be programmed to measure oxygen saturation values of a patient over a first period of time, determine if at least one oxygen saturation value obtained over the first period of time exceeds a first alarm threshold, determine whether a first alarm should be triggered based on the determination that the at least one oxygen saturation value obtained over the first period of time exceeds the first alarm threshold, determine a second alarm threshold to be applied during a second period of time subsequent to the first period of time, the second alarm threshold replacing the first alarm threshold.

11 Claims, 14 Drawing Sheets

Related U.S. Application Data continuation of application No. 15/881,602, filed on Jan. 26, 2018, now Pat. No. Re. 47,218, which is an application for the reissue of Pat. No. 9,775,570, which is a continuation of application No. 13/037,184, filed on Feb. 28, 2011, now Pat. No. 9,724,024.

(60) Provisional application No. 61/328,630, filed on Apr. 27, 2010, provisional application No. 61/309,419, filed on Mar. 1, 2010.

(52) U.S. Cl.
CPC ..... *A61B 5/14552* (2013.01); *A61B 5/74* (2013.01); *G08B 29/26* (2013.01); *A61B 2560/0276* (2013.01)

(56) References Cited

U.S. PATENT DOCUMENTS 4,425,921 A 1/1984 Fujisaki et al.
4,450,843 A 5/1984 Barney et al.
4,557,545 A 12/1985 Ohtsuki et al.
4,639,718 A 1/1987 Gasper
4,653,498 A 3/1987 New et al.
4,807,639 A 2/1989 Shimizu et al.
4,883,055 A 11/1989 Merrick
4,889,132 A 12/1989 Hutcheson et al.
4,896,676 A 1/1990 Sasaki
4,960,128 A 10/1990 Gordon et al.
4,964,408 A 10/1990 Hink et al.
4,975,684 A 12/1990 Guttinger et al.
5,041,187 A 8/1991 Hink et al.
5,069,213 A 12/1991 Polczynski
5,111,817 A 5/1992 Clark et al.
5,163,438 A 11/1992 Gordon et al.
5,226,417 A 7/1993 Swedlow et al.
5,253,645 A 10/1993 Friedman et al.
5,253,646 A 10/1993 Delpy et al.
5,285,782 A 2/1994 Prosser
5,319,355 A 6/1994 Russek
5,319,363 A 6/1994 Welch
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,464,012 A 11/1995 Falcone
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,539,706 A 7/1996 Takenaka et al.
5,561,275 A 10/1996 Savage et al.
5,562,002 A 10/1996 Lalin
5,590,649 A 1/1997 Caro et al.
5,602,924 A 2/1997 Durand et al.
5,615,684 A 4/1997 Hagel et al.
5,632,272 A 5/1997 Diab et al.
5,637,002 A 6/1997 Buck et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,685,299 A 11/1997 Diab et al.
D390,192 S 2/1998 Ono
D391,551 S 3/1998 Ono
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,793,413 A 8/1998 Hylton et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,865,736 A 2/1999 Baker, Jr. et al.
5,876,348 A 3/1999 Sugo et al.
5,890,929 A 4/1999 Mills et al.
5,904,654 A 5/1999 Wohltmann et al.
5,919,134 A 7/1999 Diab
5,919,141 A 7/1999 Money et al.
5,920,263 A 7/1999 Huttenhoff et al.
5,934,925 A 8/1999 Tobler et al.
5,940,182 A 8/1999 Lepper, Jr. et al.
5,987,343 A 11/1999 Kinast
5,995,855 A 11/1999 Kiani et al.
5,997,343 A 12/1999 Mills et al.
6,002,952 A 12/1999 Diab et al.
6,005,658 A 12/1999 Kaluza et al.
6,010,937 A 1/2000 Karam et al.
6,011,986 A 1/2000 Diab et al.
6,027,452 A 2/2000 Flaherty et al.
6,036,642 A 3/2000 Diab et al.
6,040,578 A 3/2000 Malin et al.
6,045,509 A 4/2000 Caro et al.
6,050,951 A 4/2000 Friedman et al.
6,066,204 A 5/2000 Haven
6,067,462 A 5/2000 Diab et al.
6,081,735 A 6/2000 Diab et al.
6,088,607 A 7/2000 Diab et al.
6,110,522 A 8/2000 Lepper, Jr. et al.
6,115,673 A 9/2000 Malin et al.
6,124,597 A 9/2000 Shehada
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,166,633 A 12/2000 Wang et al.
6,184,521 B1 2/2001 Coffin, IV et al.
6,190,325 B1 2/2001 Narimatsu
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,661 B1 6/2001 Schluess et al.
6,241,683 B1 6/2001 Macklem et al.
6,241,684 B1 6/2001 Amano et al.
6,253,097 B1 6/2001 Aronow et al.
6,255,708 B1 7/2001 Sudharsanan et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,280,381 B1 8/2001 Malin et al.
6,285,896 B1 9/2001 Tobler et al.
6,301,493 B1 10/2001 Marro et al.
6,308,089 B1 10/2001 von der Ruhr et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker

(56) References Cited

U.S. PATENT DOCUMENTS

| | | | |
|---|---|---|---|
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,501,975 | B2 | 12/2002 | Diab et al. |
| 6,505,059 | B1 | 1/2003 | Kollias et al. |
| 6,510,344 | B1 | 1/2003 | Halpern |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,541,756 | B2 | 4/2003 | Schulz et al. |
| 6,542,764 | B1 | 4/2003 | Al-Ali et al. |
| 6,553,242 | B1 | 4/2003 | Sarussi |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,643,530 | B2 | 11/2003 | Diab et al. |
| 6,645,155 | B2 | 11/2003 | Inukai et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,738,652 | B2 | 5/2004 | Mattu et al. |
| 6,745,060 | B2 | 6/2004 | Diab et al. |
| 6,754,516 | B2 | 6/2004 | Mannheimer |
| 6,755,689 | B2 | 6/2004 | Zhang et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,788,965 | B2 | 9/2004 | Ruchti et al. |
| 6,792,300 | B1 | 9/2004 | Diab et al. |
| 6,813,511 | B2 | 11/2004 | Diab et al. |
| 6,816,241 | B2 | 11/2004 | Grubisic |
| 6,816,266 | B2 | 11/2004 | Varshneya et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,840,904 | B2 | 1/2005 | Goldberg |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,876,931 | B2 | 4/2005 | Lorenz et al. |
| 6,897,788 | B2 | 5/2005 | Khair et al. |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,956,649 | B2 | 10/2005 | Acosta et al. |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,990,364 | B2 | 1/2006 | Ruchti et al. |
| 6,993,371 | B2 | 1/2006 | Kiani et al. |
| 6,996,427 | B2 | 2/2006 | Ali et al. |
| 6,998,247 | B2 | 2/2006 | Monfre et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,079,035 | B2 | 7/2006 | Bock et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,123,950 | B2 | 10/2006 | Mannheimer |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |

(56) References Cited

U.S. PATENT DOCUMENTS

| | | | |
|---|---|---|---|
| 7,377,899 | B2 | 5/2008 | Weber et al. |
| 7,383,070 | B2 | 6/2008 | Diab et al. |
| 7,395,158 | B2 | 7/2008 | Monfre et al. |
| 7,399,277 | B2 | 7/2008 | Saidara et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,769,436 | B1 | 8/2010 | Boileau et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,214,043 | B2 | 7/2012 | Matos |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,401,607 | B2 | 3/2013 | Mannheimer |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |

(56) References Cited

U.S. PATENT DOCUMENTS

| | | | |
|---|---|---|---|
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,554,297 | B2 | 10/2013 | Moon et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,597,274 | B2 | 12/2013 | Sloan et al. |
| 8,600,467 | B2 | 12/2013 | Al-Ali et al. |
| 8,606,342 | B2 | 12/2013 | Diab |
| 8,622,902 | B2 | 1/2014 | Woehrle |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | Macneish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |
| 8,790,268 | B2 | 7/2014 | Al-Ali |
| 8,792,949 | B2 | 7/2014 | Baker, Jr. |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,838,196 | B2 | 9/2014 | Mannheimer |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,115 | B2 | 10/2014 | Muir |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,956,294 | B2 | 2/2015 | McCombie et al. |
| 8,961,416 | B2 | 2/2015 | Siddiqui et al. |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,407 | B1 | 5/2015 | Bennett-Guerrero |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |

(56) References Cited

U.S. PATENT DOCUMENTS

| | | | |
|---|---|---|---|
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-Ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,692 | B2 | 4/2017 | Lamego et al. |
| 9,622,693 | B2 | 4/2017 | Diab |
| D788,312 | S | 5/2017 | Al-Ali et al. |
| 9,636,055 | B2 | 5/2017 | Al-Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |
| 9,668,703 | B2 | 6/2017 | Al-Ali |
| 9,675,286 | B2 | 6/2017 | Diab |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,717,425 | B2 | 8/2017 | Kiani et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| 9,750,442 | B2 | 9/2017 | Olsen |
| 9,750,443 | B2 | 9/2017 | Smith et al. |
| 9,750,461 | B1 | 9/2017 | Telfort |
| 9,775,545 | B2 | 10/2017 | Al-Ali et al. |
| 9,775,546 | B2 | 10/2017 | Diab et al. |
| 9,775,570 | B2 | 10/2017 | Al-Ali |
| 9,778,079 | B1 | 10/2017 | Al-Ali et al. |
| 9,782,077 | B2 | 10/2017 | Lamego et al. |
| 9,782,110 | B2 | 10/2017 | Kiani |
| 9,787,568 | B2 | 10/2017 | Lamego et al. |
| 9,788,735 | B2 | 10/2017 | Al-Ali |
| 9,788,768 | B2 | 10/2017 | Al-Ali et al. |
| 9,795,300 | B2 | 10/2017 | Al-Ali |
| 9,795,310 | B2 | 10/2017 | Al-Ali |
| 9,795,358 | B2 | 10/2017 | Telfort et al. |
| 9,795,739 | B2 | 10/2017 | Al-Ali et al. |
| 9,801,556 | B2 | 10/2017 | Kiani |
| 9,801,588 | B2 | 10/2017 | Weber et al. |
| 9,808,188 | B1 | 11/2017 | Perea et al. |
| 9,814,418 | B2 | 11/2017 | Weber et al. |
| 9,820,691 | B2 | 11/2017 | Kiani |
| 9,833,152 | B2 | 12/2017 | Kiani et al. |
| 9,833,180 | B2 | 12/2017 | Shakespeare et al. |
| 9,839,379 | B2 | 12/2017 | Al-Ali et al. |
| 9,839,381 | B1 | 12/2017 | Weber et al. |
| 9,847,002 | B2 | 12/2017 | Kiani et al. |
| 9,847,749 | B2 | 12/2017 | Kiani et al. |
| 9,848,800 | B1 | 12/2017 | Lee et al. |
| 9,848,806 | B2 | 12/2017 | Al-Ali et al. |
| 9,848,807 | B2 | 12/2017 | Lamego |
| 9,861,298 | B2 | 1/2018 | Eckerbom et al. |
| 9,861,304 | B2 | 1/2018 | Al-Ali et al. |
| 9,861,305 | B1 | 1/2018 | Weber et al. |
| 9,867,578 | B2 | 1/2018 | Al-Ali et al. |
| 9,872,623 | B2 | 1/2018 | Al-Ali |
| 9,876,320 | B2 | 1/2018 | Coverston et al. |
| 9,877,650 | B2 | 1/2018 | Muhsin et al. |
| 9,877,686 | B2 | 1/2018 | Al-Ali et al. |
| 9,891,079 | B2 | 2/2018 | Dalvi |
| 9,895,107 | B2 | 2/2018 | Al-Ali et al. |
| 9,913,617 | B2 | 3/2018 | Al-Ali et al. |
| 9,924,893 | B2 | 3/2018 | Schurman et al. |
| 9,924,897 | B1 | 3/2018 | Abdul-Hafiz |
| 9,936,917 | B2 | 4/2018 | Poeze et al. |
| 9,943,269 | B2 | 4/2018 | Muhsin et al. |
| 9,949,676 | B2 | 4/2018 | Al-Ali |
| 9,955,937 | B2 | 5/2018 | Telfort |
| 9,965,946 | B2 | 5/2018 | Al-Ali |
| 9,980,667 | B2 | 5/2018 | Kiani et al. |
| D820,865 | S | 6/2018 | Muhsin et al. |
| 9,986,919 | B2 | 6/2018 | Lamego et al. |
| 9,986,952 | B2 | 6/2018 | Dalvi et al. |
| 9,989,560 | B2 | 6/2018 | Poeze et al. |
| 9,993,207 | B2 | 6/2018 | Al-Ali et al. |
| 10,007,758 | B2 | 6/2018 | Al-Ali et al. |
| D822,215 | S | 7/2018 | Al-Ali et al. |
| D822,216 | S | 7/2018 | Barker et al. |
| 10,010,276 | B2 | 7/2018 | Al-Ali et al. |
| 10,032,002 | B2 | 7/2018 | Kiani et al. |
| 10,039,482 | B2 | 8/2018 | Al-Ali et al. |
| 10,052,037 | B2 | 8/2018 | Kinast et al. |
| 10,058,275 | B2 | 8/2018 | Al-Ali et al. |
| 10,064,562 | B2 | 9/2018 | Al-Ali |
| 10,086,138 | B1 | 10/2018 | Novak, Jr. |
| 10,092,200 | B2 | 10/2018 | Al-Ali et al. |
| 10,092,249 | B2 | 10/2018 | Kiani et al. |
| 10,098,550 | B2 | 10/2018 | Al-Ali et al. |
| 10,098,591 | B2 | 10/2018 | Al-Ali et al. |
| 10,098,610 | B2 | 10/2018 | Al-Ali et al. |
| 10,111,591 | B2 | 10/2018 | Dyell et al. |
| D833,624 | S | 11/2018 | DeJong et al. |
| 10,123,726 | B2 | 11/2018 | Al-Ali et al. |
| 10,123,729 | B2 | 11/2018 | Dyell et al. |
| 10,130,289 | B2 | 11/2018 | Al-Ali et al. |
| 10,130,291 | B2 | 11/2018 | Schurman et al. |
| D835,282 | S | 12/2018 | Barker et al. |
| D835,283 | S | 12/2018 | Barker et al. |
| D835,284 | S | 12/2018 | Barker et al. |
| D835,285 | S | 12/2018 | Barker et al. |

(56) References Cited

U.S. PATENT DOCUMENTS

| | | | |
|---|---|---|---|
| 10,149,616 | B2 | 12/2018 | Al-Ali et al. |
| 10,154,815 | B2 | 12/2018 | Al-Ali et al. |
| 10,159,412 | B2 | 12/2018 | Lamego et al. |
| 10,188,296 | B2 | 1/2019 | Al-Ali et al. |
| 10,188,331 | B1 | 1/2019 | Al-Ali et al. |
| 10,188,348 | B2 | 1/2019 | Kiani et al. |
| RE47,218 | E | 2/2019 | Al-Ali |
| RE47,244 | E | 2/2019 | Kiani et al. |
| RE47,249 | E | 2/2019 | Kiani et al. |
| 10,194,847 | B2 | 2/2019 | Al-Ali |
| 10,194,848 | B1 | 2/2019 | Kiani et al. |
| 10,201,298 | B2 | 2/2019 | Al-Ali et al. |
| 10,205,272 | B2 | 2/2019 | Kiani et al. |
| 10,205,291 | B2 | 2/2019 | Scruggs et al. |
| 10,213,108 | B2 | 2/2019 | Al-Ali |
| 10,219,706 | B2 | 3/2019 | Al-Ali |
| 10,219,746 | B2 | 3/2019 | McHale et al. |
| 10,226,187 | B2 | 3/2019 | Al-Ali et al. |
| 10,226,576 | B2 | 3/2019 | Kiani |
| 10,231,657 | B2 | 3/2019 | Al-Ali et al. |
| 10,231,670 | B2 | 3/2019 | Blank et al. |
| 10,231,676 | B2 | 3/2019 | Al-Ali et al. |
| RE47,353 | E | 4/2019 | Kiani et al. |
| 10,251,585 | B2 | 4/2019 | Al-Ali et al. |
| 10,251,586 | B2 | 4/2019 | Lamego |
| 10,255,994 | B2 | 4/2019 | Sampath et al. |
| 10,258,265 | B1 | 4/2019 | Poeze et al. |
| 10,258,266 | B1 | 4/2019 | Poeze et al. |
| 10,271,748 | B2 | 4/2019 | Al-Ali |
| 10,278,626 | B2 | 5/2019 | Schurman et al. |
| 10,278,648 | B2 | 5/2019 | Al-Ali et al. |
| 10,279,247 | B2 | 5/2019 | Kiani |
| 10,292,628 | B1 | 5/2019 | Poeze et al. |
| 10,292,657 | B2 | 5/2019 | Abdul-Hafiz et al. |
| 10,292,664 | B2 | 5/2019 | Al-Ali |
| 10,299,708 | B1 | 5/2019 | Poeze et al. |
| 10,299,709 | B2 | 5/2019 | Perea et al. |
| 10,299,720 | B2 | 5/2019 | Brown et al. |
| 10,305,775 | B2 | 5/2019 | Lamego et al. |
| 10,307,111 | B2 | 6/2019 | Muhsin et al. |
| 10,325,681 | B2 | 6/2019 | Sampath et al. |
| 10,327,337 | B2 | 6/2019 | Triman et al. |
| 10,327,713 | B2 | 6/2019 | Barker et al. |
| 10,332,630 | B2 | 6/2019 | Al-Ali |
| 10,335,033 | B2 | 7/2019 | Al-Ali |
| 10,335,068 | B2 | 7/2019 | Poeze et al. |
| 10,335,072 | B2 | 7/2019 | Al-Ali et al. |
| 10,342,470 | B2 | 7/2019 | Al-Ali et al. |
| 10,342,487 | B2 | 7/2019 | Al-Ali et al. |
| 10,342,497 | B2 | 7/2019 | Al-Ali et al. |
| 10,349,895 | B2 | 7/2019 | Telfort et al. |
| 10,349,898 | B2 | 7/2019 | Al-Ali et al. |
| 10,354,504 | B2 | 7/2019 | Kiani et al. |
| 10,357,206 | B2 | 7/2019 | Weber et al. |
| 10,357,209 | B2 | 7/2019 | Al-Ali |
| 10,366,787 | B2 | 7/2019 | Sampath et al. |
| 10,368,787 | B2 | 8/2019 | Reichgott et al. |
| 10,376,190 | B1 | 8/2019 | Poeze et al. |
| 10,376,191 | B1 | 8/2019 | Poeze et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| 10,398,320 | B2 | 9/2019 | Kiani et al. |
| 10,405,804 | B2 | 9/2019 | Al-Ali |
| 10,413,666 | B2 | 9/2019 | Al-Ali et al. |
| 10,420,493 | B2 | 9/2019 | Al-Ali et al. |
| D864,120 | S | 10/2019 | Forrest et al. |
| 10,433,776 | B2 | 10/2019 | Al-Ali |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali |
| 10,456,038 | B2 | 10/2019 | Lamego et al. |
| 10,463,284 | B2 | 11/2019 | Al-Ali et al. |
| 10,463,340 | B2 | 11/2019 | Telfort et al. |
| 10,470,695 | B2 | 11/2019 | Al-Ali |
| 10,471,159 | B1 | 11/2019 | Lapotko et al. |
| 10,478,107 | B2 | 11/2019 | Kiani et al. |
| 10,503,379 | B2 | 12/2019 | Al-Ali et al. |
| 10,505,311 | B2 | 12/2019 | Al-Ali et al. |
| 10,512,436 | B2 | 12/2019 | Muhsin et al. |
| 10,524,706 | B2 | 1/2020 | Telfort et al. |
| 10,524,738 | B2 | 1/2020 | Olsen |
| 10,531,811 | B2 | 1/2020 | Al-Ali et al. |
| 10,531,819 | B2 | 1/2020 | Diab et al. |
| 10,531,835 | B2 | 1/2020 | Al-Ali et al. |
| 10,532,174 | B2 | 1/2020 | Al-Ali |
| 10,537,285 | B2 | 1/2020 | Sherim et al. |
| 10,542,903 | B2 | 1/2020 | Al-Ali et al. |
| 10,548,561 | B2 | 2/2020 | Telfort et al. |
| 10,555,678 | B2 | 2/2020 | Dalvi et al. |
| 10,568,514 | B2 | 2/2020 | Wojtczuk et al. |
| 10,568,553 | B2 | 2/2020 | O'Neil et al. |
| RE47,882 | E | 3/2020 | Al-Ali |
| 10,575,779 | B2 | 3/2020 | Poeze et al. |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf et al. |
| D906,970 | S | 1/2021 | Forrest et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| D916,135 | S | 4/2021 | Indorf et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0058864 | A1 | 5/2002 | Mansfield et al. |
| 2002/0098807 | A1 | 7/2002 | Saarnimo |
| 2002/0133080 | A1 | 9/2002 | Apruzzese et al. |
| 2003/0013975 | A1 | 1/2003 | Kiani |
| 2003/0018241 | A1* | 1/2003 | Mannheimer ..... A61B 5/14551 600/300 |
| 2003/0018243 | A1 | 1/2003 | Gerhardt et al. |
| 2003/0135087 | A1 | 7/2003 | Hickle et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0106163 | A1 | 6/2004 | Workman, Jr. et al. |
| 2004/0162499 | A1 | 8/2004 | Nagai et al. |
| 2005/0027182 | A1 | 2/2005 | Siddiqui |
| 2005/0038332 | A1 | 2/2005 | Saidara et al. |
| 2005/0055276 | A1 | 3/2005 | Kiani et al. |

(56) References Cited

U.S. PATENT DOCUMENTS

2005/0177096 A1 8/2005 Bollish
2005/0234317 A1 10/2005 Kiani
2005/0240091 A1 10/2005 Lynn
2006/0073719 A1 4/2006 Kiani
2006/0189871 A1 8/2006 Al-Ali et al.
2006/0220881 A1 10/2006 Al-Ali
2007/0040692 A1 2/2007 Smith et al.
2007/0073116 A1 3/2007 Kiani et al.
2007/0156031 A1* 7/2007 Sullivan ..... A61B 5/7282 600/300
2007/0180140 A1 8/2007 Welch et al.
2007/0244377 A1 10/2007 Cozad et al.
2007/0282478 A1 12/2007 Al-Ali et al.
2008/0064965 A1 3/2008 Jay et al.
2008/0094228 A1 4/2008 Welch et al.
2008/0103375 A1 5/2008 Kiani
2008/0157980 A1 7/2008 Sachanandani et al.
2008/0162182 A1* 7/2008 Cazares ..... G16H 50/30 705/2
2008/0183054 A1 7/2008 Kroeger et al.
2008/0221418 A1 9/2008 Al-Ali et al.
2008/0255438 A1 10/2008 Saidara
2008/0281168 A1 11/2008 Gibson
2008/0287756 A1 11/2008 Lynn
2009/0036759 A1 2/2009 Ault et al.
2009/0040874 A1 2/2009 Rooney
2009/0093687 A1 4/2009 Telfort et al.
2009/0095926 A1 4/2009 MacNeish, III
2009/0210163 A1 8/2009 Ochs et al.
2009/0247848 A1* 10/2009 Baker, Jr. ..... A61B 5/14551 600/323
2009/0247849 A1 10/2009 McCutcheon et al.
2009/0247851 A1 10/2009 Batchelder et al.
2009/0247924 A1 10/2009 Lamego et al.
2009/0247984 A1 10/2009 Lamego et al.
2009/0275807 A1 11/2009 Sitzman et al.
2009/0275813 A1 11/2009 Davis
2009/0275844 A1 11/2009 Al-Ali
2009/0299157 A1 12/2009 Telfort et al.
2009/0326340 A1 12/2009 Wang et al.
2010/0004518 A1 1/2010 Vo et al.
2010/0030040 A1 2/2010 Poeze et al.
2010/0099964 A1 4/2010 O'Reilly et al.
2010/0113904 A1 5/2010 Batchelder et al.
2010/0234718 A1 9/2010 Sampath et al.
2010/0261979 A1 10/2010 Kiani
2010/0270257 A1 10/2010 Wachman et al.
2011/0001605 A1 1/2011 Kiani et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0105854 A1 5/2011 Kiani et al.
2011/0118561 A1 5/2011 Tari et al.
2011/0125060 A1 5/2011 Telfort et al.
2011/0137297 A1 6/2011 Kiani et al.
2011/0172498 A1 7/2011 Olsen et al.
2011/0208015 A1 8/2011 Welch et al.
2011/0209915 A1 9/2011 Telfort et al.
2011/0213212 A1 9/2011 Al-Ali
2011/0230733 A1 9/2011 Al-Ali
2011/0237911 A1 9/2011 Lamego et al.
2011/0237969 A1 9/2011 Eckerbom et al.
2011/0288383 A1 11/2011 Diab
2012/0041316 A1 2/2012 Al Ali et al.
2012/0046557 A1 2/2012 Kiani
2012/0059267 A1 3/2012 Lamego et al.
2012/0088984 A1 4/2012 Al-Ali et al.
2012/0116175 A1 5/2012 Al-Ali et al.
2012/0123231 A1 5/2012 O'Reilly
2012/0165629 A1 6/2012 Merritt et al.
2012/0179006 A1 7/2012 Jansen et al.
2012/0209082 A1 8/2012 Al-Ali
2012/0209084 A1 8/2012 Olsen et al.
2012/0226117 A1 9/2012 Lamego et al.
2012/0227739 A1 9/2012 Kiani
2012/0232366 A1 9/2012 Kiani
2012/0265039 A1 10/2012 Kiani
2012/0283524 A1 11/2012 Kiani et al.
2012/0286955 A1 11/2012 Welch et al.
2012/0296178 A1 11/2012 Lamego et al.
2012/0319816 A1 12/2012 Al-Ali
2012/0330112 A1 12/2012 Lamego et al.
2013/0023775 A1 1/2013 Lamego et al.
2013/0041591 A1 2/2013 Lamego
2013/0045685 A1 2/2013 Kiani
2013/0046204 A1 2/2013 Lamego et al.
2013/0060108 A1 3/2013 Schurman et al.
2013/0060147 A1 3/2013 Welch et al.
2013/0096405 A1 4/2013 Garfio
2013/0096936 A1 4/2013 Sampath et al.
2013/0109935 A1 5/2013 Al-Ali et al.
2013/0162433 A1 6/2013 Muhsin et al.
2013/0190581 A1 7/2013 Al-Ali et al.
2013/0197328 A1 8/2013 Diab et al.
2013/0211214 A1 8/2013 Olsen
2013/0243021 A1 9/2013 Siskavich
2013/0253334 A1 9/2013 Al-Ali et al.
2013/0267804 A1 10/2013 Al-Ali
2013/0274571 A1 10/2013 Diab et al.
2013/0274572 A1 10/2013 Al-Ali et al.
2013/0296672 A1 11/2013 O'Neil et al.
2013/0296713 A1 11/2013 Al-Ali et al.
2013/0317370 A1 11/2013 Dalvi et al.
2013/0324808 A1 12/2013 Al-Ali et al.
2013/0331660 A1 12/2013 Al-Ali et al.
2013/0331670 A1 12/2013 Kiani
2013/0338461 A1 12/2013 Lamego et al.
2013/0345921 A1 12/2013 Al-Ali et al.
2014/0012100 A1 1/2014 Al-Ali et al.
2014/0025306 A1 1/2014 Weber et al.
2014/0034353 A1 2/2014 Al-Ali et al.
2014/0051952 A1 2/2014 Reichgott et al.
2014/0051953 A1 2/2014 Lamego et al.
2014/0051954 A1 2/2014 Al-Ali et al.
2014/0058230 A1 2/2014 Abdul-Hafiz et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0094667 A1 4/2014 Schurman et al.
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0121483 A1 5/2014 Kiani
2014/0125495 A1 5/2014 Al-Ali
2014/0127137 A1 5/2014 Bellott et al.
2014/0128696 A1 5/2014 Al-Ali
2014/0128699 A1 5/2014 Al-Ali et al.
2014/0129702 A1 5/2014 Lamego et al.
2014/0135588 A1 5/2014 Al-Ali et al.
2014/0142401 A1 5/2014 Al-Ali et al.
2014/0142402 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0194709 A1 7/2014 Al-Ali et al.
2014/0194711 A1 7/2014 Al-Ali
2014/0194766 A1 7/2014 Al-Ali et al.
2014/0200420 A1 7/2014 Al-Ali
2014/0200422 A1 7/2014 Weber et al.
2014/0206963 A1 7/2014 Al-Ali
2014/0213864 A1 7/2014 Abdul-Hafiz et al.
2014/0243627 A1 8/2014 Diab et al.
2014/0266790 A1 9/2014 Al-Ali et al.
2014/0275808 A1 9/2014 Poeze et al.
2014/0275835 A1 9/2014 Lamego et al.

(56) References Cited

U.S. PATENT DOCUMENTS

| | | | |
|---|---|---|---|
| 2014/0275871 | A1 | 9/2014 | Lamego et al. |
| 2014/0275872 | A1 | 9/2014 | Merritt et al. |
| 2014/0275881 | A1 | 9/2014 | Lamego et al. |
| 2014/0276115 | A1 | 9/2014 | Dalvi et al. |
| 2014/0288400 | A1 | 9/2014 | Diab et al. |
| 2014/0296664 | A1 | 10/2014 | Bruinsma et al. |
| 2014/0303520 | A1 | 10/2014 | Telfort et al. |
| 2014/0309506 | A1 | 10/2014 | Lamego et al. |
| 2014/0309507 | A1 | 10/2014 | Baker, Jr. |
| 2014/0309559 | A1 | 10/2014 | Telfort et al. |
| 2014/0316217 | A1 | 10/2014 | Purdon et al. |
| 2014/0316218 | A1 | 10/2014 | Purdon et al. |
| 2014/0316228 | A1 | 10/2014 | Blank et al. |
| 2014/0323825 | A1 | 10/2014 | Al-Ali et al. |
| 2014/0323897 | A1 | 10/2014 | Brown et al. |
| 2014/0323898 | A1 | 10/2014 | Purdon et al. |
| 2014/0330092 | A1 | 11/2014 | Al-Ali et al. |
| 2014/0330098 | A1 | 11/2014 | Merritt et al. |
| 2014/0330099 | A1 | 11/2014 | Al-Ali et al. |
| 2014/0333440 | A1 | 11/2014 | Kiani |
| 2014/0336481 | A1 | 11/2014 | Shakespeare et al. |
| 2014/0343436 | A1 | 11/2014 | Kiani |
| 2015/0005600 | A1 | 1/2015 | Blank et al. |
| 2015/0011907 | A1 | 1/2015 | Purdon et al. |
| 2015/0012231 | A1 | 1/2015 | Poeze et al. |
| 2015/0018650 | A1 | 1/2015 | Al-Ali et al. |
| 2015/0025406 | A1 | 1/2015 | Al-Ali |
| 2015/0032029 | A1 | 1/2015 | Al-Ali et al. |
| 2015/0038859 | A1 | 2/2015 | Dalvi et al. |
| 2015/0045637 | A1 | 2/2015 | Dalvi |
| 2015/0051462 | A1 | 2/2015 | Olsen |
| 2015/0073241 | A1 | 3/2015 | Lamego |
| 2015/0080754 | A1 | 3/2015 | Purdon et al. |
| 2015/0087936 | A1 | 3/2015 | Al-Ali et al. |
| 2015/0094546 | A1 | 4/2015 | Al-Ali |
| 2015/0097701 | A1 | 4/2015 | Al-Ali et al. |
| 2015/0099950 | A1 | 4/2015 | Al-Ali et al. |
| 2015/0099951 | A1 | 4/2015 | Al-Ali et al. |
| 2015/0099955 | A1 | 4/2015 | Al-Ali et al. |
| 2015/0101844 | A1 | 4/2015 | Al-Ali et al. |
| 2015/0106121 | A1 | 4/2015 | Muhsin et al. |
| 2015/0112151 | A1 | 4/2015 | Muhsin et al. |
| 2015/0116076 | A1 | 4/2015 | Al-Ali et al. |
| 2015/0126830 | A1 | 5/2015 | Schurman et al. |
| 2015/0133755 | A1 | 5/2015 | Smith et al. |
| 2015/0141781 | A1 | 5/2015 | Weber et al. |
| 2015/0165312 | A1 | 6/2015 | Kiani |
| 2015/0196237 | A1 | 7/2015 | Lamego |
| 2015/0216459 | A1 | 8/2015 | Al-Ali et al. |
| 2015/0230755 | A1 | 8/2015 | Al-Ali et al. |
| 2015/0238722 | A1 | 8/2015 | Al-Ali |
| 2015/0245773 | A1 | 9/2015 | Lamego et al. |
| 2015/0245794 | A1 | 9/2015 | Al-Ali |
| 2015/0257689 | A1 | 9/2015 | Al-Ali et al. |
| 2015/0272514 | A1 | 10/2015 | Kiani et al. |
| 2015/0351697 | A1 | 12/2015 | Weber et al. |
| 2015/0351704 | A1 | 12/2015 | Kiani et al. |
| 2015/0359429 | A1 | 12/2015 | Al-Ali et al. |
| 2015/0366472 | A1 | 12/2015 | Kiani |
| 2015/0366507 | A1 | 12/2015 | Blank |
| 2015/0374298 | A1 | 12/2015 | Al-Ali et al. |
| 2015/0380875 | A1 | 12/2015 | Coverston et al. |
| 2016/0000362 | A1 | 1/2016 | Diab et al. |
| 2016/0007930 | A1 | 1/2016 | Weber et al. |
| 2016/0029932 | A1 | 2/2016 | Al-Ali |
| 2016/0045118 | A1 | 2/2016 | Kiani |
| 2016/0051205 | A1 | 2/2016 | Al-Ali et al. |
| 2016/0058338 | A1 | 3/2016 | Schurman et al. |
| 2016/0058347 | A1 | 3/2016 | Reichgott et al. |
| 2016/0066823 | A1 | 3/2016 | Al-Ali et al. |
| 2016/0066824 | A1 | 3/2016 | Al-Ali et al. |
| 2016/0066879 | A1 | 3/2016 | Telfort et al. |
| 2016/0072429 | A1 | 3/2016 | Kiani et al. |
| 2016/0081552 | A1 | 3/2016 | Wojtczuk et al. |
| 2016/0095543 | A1 | 4/2016 | Telfort et al. |
| 2016/0095548 | A1 | 4/2016 | Al-Ali et al. |
| 2016/0103598 | A1 | 4/2016 | Al-Ali et al. |
| 2016/0113527 | A1 | 4/2016 | Al-Ali et al. |
| 2016/0143548 | A1 | 5/2016 | Al-Ali |
| 2016/0166182 | A1 | 6/2016 | Al-Ali et al. |
| 2016/0166183 | A1 | 6/2016 | Poeze et al. |
| 2016/0166188 | A1 | 6/2016 | Bruinsma et al. |
| 2016/0166210 | A1 | 6/2016 | Al-Ali |
| 2016/0192869 | A1 | 7/2016 | Kiani et al. |
| 2016/0196388 | A1 | 7/2016 | Lamego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0007134 | A1 | 1/2017 | Al-Ali et al. |
| 2017/0007190 | A1 | 1/2017 | Al-Ali et al. |
| 2017/0007198 | A1 | 1/2017 | Al-Ali et al. |
| 2017/0014083 | A1 | 1/2017 | Diab et al. |
| 2017/0014084 | A1 | 1/2017 | Al-Ali et al. |
| 2017/0021099 | A1 | 1/2017 | Al-Ali et al. |
| 2017/0024748 | A1 | 1/2017 | Haider |
| 2017/0027456 | A1 | 2/2017 | Kinast et al. |
| 2017/0042488 | A1 | 2/2017 | Muhsin |
| 2017/0055847 | A1 | 3/2017 | Kiani et al. |
| 2017/0055851 | A1 | 3/2017 | Al-Ali |
| 2017/0055882 | A1 | 3/2017 | Al-Ali et al. |
| 2017/0055887 | A1 | 3/2017 | Al-Ali |
| 2017/0055896 | A1 | 3/2017 | Al-Ali et al. |
| 2017/0079594 | A1 | 3/2017 | Telfort et al. |
| 2017/0086723 | A1 | 3/2017 | Al-Ali et al. |
| 2017/0143281 | A1 | 5/2017 | Olsen |
| 2017/0147774 | A1 | 5/2017 | Kiani |
| 2017/0156620 | A1 | 6/2017 | Al-Ali et al. |
| 2017/0173632 | A1 | 6/2017 | Al-Ali |
| 2017/0187146 | A1 | 6/2017 | Kiani et al. |
| 2017/0188919 | A1 | 7/2017 | Al-Ali et al. |
| 2017/0196464 | A1 | 7/2017 | Jansen et al. |
| 2017/0196470 | A1 | 7/2017 | Lamego et al. |
| 2017/0202490 | A1 | 7/2017 | Al-Ali et al. |
| 2017/0224231 | A1 | 8/2017 | Al-Ali |
| 2017/0224262 | A1 | 8/2017 | Al-Ali |
| 2017/0228516 | A1 | 8/2017 | Sampath et al. |
| 2017/0245790 | A1 | 8/2017 | Al-Ali et al. |
| 2017/0251974 | A1 | 9/2017 | Shreim et al. |
| 2017/0251975 | A1 | 9/2017 | Shreim et al. |
| 2017/0258403 | A1 | 9/2017 | Abdul-Hafiz et al. |
| 2017/0311891 | A1 | 11/2017 | Kiani et al. |
| 2017/0325728 | A1 | 11/2017 | Al-Ali et al. |
| 2017/0332976 | A1 | 11/2017 | Al-Ali et al. |
| 2017/0340293 | A1 | 11/2017 | Al-Ali et al. |
| 2017/0360310 | A1 | 12/2017 | Kiani et al. |
| 2017/0367632 | A1 | 12/2017 | Al-Ali et al. |
| 2018/0008146 | A1 | 1/2018 | Al-Ali et al. |
| 2018/0013562 | A1 | 1/2018 | Haider et al. |
| 2018/0014752 | A1 | 1/2018 | Al-Ali et al. |
| 2018/0028124 | A1 | 2/2018 | Al-Ali et al. |
| 2018/0055390 | A1 | 3/2018 | Kiani et al. |
| 2018/0055430 | A1 | 3/2018 | Diab et al. |
| 2018/0064381 | A1 | 3/2018 | Shakespeare et al. |
| 2018/0070867 | A1 | 3/2018 | Smith et al. |
| 2018/0082767 | A1 | 3/2018 | Al-Ali et al. |
| 2018/0085068 | A1 | 3/2018 | Telfort |
| 2018/0087937 | A1 | 3/2018 | Al-Ali et al. |
| 2018/0103874 | A1 | 4/2018 | Lee et al. |
| 2018/0103905 | A1 | 4/2018 | Kiani |

(56) References Cited

U.S. PATENT DOCUMENTS

2018/0125368 A1 5/2018 Lamego et al.
2018/0125430 A1 5/2018 Al-Ali et al.
2018/0125445 A1 5/2018 Telfort et al.
2018/0132769 A1 5/2018 Weber et al.
2018/0146901 A1 5/2018 Al-Ali et al.
2018/0146902 A1 5/2018 Kiani et al.
2018/0153442 A1 6/2018 Eckerbom et al.
2018/0153446 A1 6/2018 Kiani
2018/0153447 A1 6/2018 Al-Ali et al.
2018/0153448 A1 6/2018 Weber et al.
2018/0168491 A1 6/2018 Al-Ali et al.
2018/0184917 A1 7/2018 Kiani
2018/0192924 A1 7/2018 Al-Ali
2018/0192953 A1 7/2018 Shreim et al.
2018/0199871 A1 7/2018 Pauley et al.
2018/0206795 A1 7/2018 Al-Ali
2018/0206815 A1 7/2018 Telfort
2018/0213583 A1 7/2018 Al-Ali
2018/0214090 A1 8/2018 Al-Ali et al.
2018/0216370 A1 8/2018 Ishiguro et al.
2018/0218792 A1 8/2018 Muhsin et al.
2018/0225960 A1 8/2018 Al-Ali et al.
2018/0238718 A1 8/2018 Dalvi
2018/0242853 A1 8/2018 Al-Ali
2018/0242921 A1 8/2018 Muhsin et al.
2018/0242923 A1 8/2018 Al-Ali et al.
2018/0242926 A1 8/2018 Muhsin et al.
2018/0247353 A1 8/2018 Al-Ali et al.
2018/0247712 A1 8/2018 Muhsin et al.
2018/0256087 A1 9/2018 Al-Ali et al.
2018/0285094 A1 10/2018 Housel et al.
2018/0289325 A1 10/2018 Poeze et al.
2018/0296161 A1 10/2018 Shreim et al.
2018/0300919 A1 10/2018 Muhsin et al.
2018/0310822 A1 11/2018 Indorf et al.
2018/0310823 A1 11/2018 Al-Ali et al.
2018/0317826 A1 11/2018 Muhsin
2018/0317841 A1 11/2018 Novak, Jr.
2018/0333055 A1 11/2018 Lamego et al.
2018/0333087 A1 11/2018 Al-Ali
2019/0000317 A1 1/2019 Muhsin et al.
2019/0000362 A1 1/2019 Kiani et al.
2019/0015023 A1 1/2019 Monfre
2019/0029574 A1 1/2019 Schurman et al.
2019/0029578 A1 1/2019 Al-Ali et al.
2019/0058280 A1 2/2019 Al-Ali et al.
2019/0058281 A1 2/2019 Al-Ali et al.
2019/0069813 A1 3/2019 Al-Ali
2019/0069814 A1 3/2019 Al-Ali
2019/0076028 A1 3/2019 Al-Ali et al.
2019/0082979 A1 3/2019 Al-Ali et al.
2019/0090760 A1 3/2019 Kinast et al.
2019/0090764 A1 3/2019 Al-Ali
2019/0117070 A1 4/2019 Muhsin et al.
2019/0117139 A1 4/2019 Al-Ali et al.
2019/0117140 A1 4/2019 Al-Ali et al.
2019/0117141 A1 4/2019 Al-Ali
2019/0117930 A1 4/2019 Al-Ali
2019/0122763 A1 4/2019 Sampath et al.
2019/0133525 A1 5/2019 Al-Ali et al.
2019/0142283 A1 5/2019 Lamego et al.
2019/0142344 A1 5/2019 Telfort et al.
2019/0150856 A1 5/2019 Kiani et al.
2019/0167161 A1 6/2019 Al-Ali et al.
2019/0175019 A1 6/2019 Al-Ali et al.
2019/0192076 A1 6/2019 McHale et al.
2019/0200941 A1 7/2019 Chandran et al.
2019/0201623 A1 7/2019 Kiani
2019/0209025 A1 7/2019 Al-Ali
2019/0214778 A1 7/2019 Scruggs et al.
2019/0216319 A1 7/2019 Poeze et al.
2019/0216379 A1 7/2019 Al-Ali et al.
2019/0221966 A1 7/2019 Kiani et al.
2019/0223804 A1 7/2019 Blank et al.
2019/0231199 A1 8/2019 Al-Ali et al.
2019/0231241 A1 8/2019 Al-Ali et al.
2019/0231270 A1 8/2019 Abdul-Hafiz et al.
2019/0239787 A1 8/2019 Pauley et al.
2019/0239824 A1 8/2019 Muhsin et al.
2019/0254578 A1 8/2019 Lamego
2019/0261857 A1 8/2019 Al-Ali
2019/0269370 A1 9/2019 Al-Ali et al.
2019/0274606 A1 9/2019 Kiani et al.
2019/0274627 A1 9/2019 Al-Ali et al.
2019/0274635 A1 9/2019 Al-Ali et al.
2019/0290136 A1 9/2019 Dalvi et al.
2019/0298270 A1 10/2019 Al-Ali et al.
2019/0304601 A1 10/2019 Sampath et al.
2019/0304605 A1 10/2019 Al-Ali
2019/0307377 A1 10/2019 Perea et al.
2019/0320906 A1 10/2019 Olsen
2019/0320959 A1 10/2019 Al-Ali
2019/0320988 A1 10/2019 Ahmed et al.
2019/0325722 A1 10/2019 Kiani et al.
2019/0350506 A1 11/2019 Al-Ali
2019/0357812 A1 11/2019 Poeze et al.
2019/0357813 A1 11/2019 Poeze et al.
2019/0357823 A1 11/2019 Reichgott et al.
2019/0357824 A1 11/2019 Al-Ali
2019/0358524 A1 11/2019 Kiani
2019/0365294 A1 12/2019 Poeze et al.
2019/0365295 A1 12/2019 Poeze et al.
2019/0374135 A1 12/2019 Poeze et al.
2019/0374139 A1 12/2019 Kiani et al.
2019/0374173 A1 12/2019 Kiani et al.
2019/0374713 A1 12/2019 Kiani et al.
2019/0386908 A1 12/2019 Lamego et al.
2019/0388039 A1 12/2019 Al-Ali
2020/0000338 A1 1/2020 Lamego et al.
2020/0000415 A1 1/2020 Barker et al.
2020/0015716 A1 1/2020 Poeze et al.
2020/0021930 A1 1/2020 Iswanto et al.
2020/0029867 A1 1/2020 Poeze et al.
2020/0037453 A1 1/2020 Triman et al.
2020/0037891 A1 2/2020 Kiani et al.
2020/0037966 A1 2/2020 Al-Ali
2020/0046257 A1 2/2020 Eckerbom et al.
2020/0054253 A1 2/2020 Al-Ali et al.
2020/0060591 A1 2/2020 Diab et al.
2020/0060628 A1 2/2020 Al-Ali et al.
2020/0060629 A1 2/2020 Muhsin et al.
2020/0060869 A1 2/2020 Telfort et al.
2020/0074819 A1 3/2020 Muhsin et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0161465 A1 6/2021 Barker et al.
2021/0236729 A1 8/2021 Kiani et al.

(56) References Cited

U.S. PATENT DOCUMENTS

| | | | |
|---|---|---|---|
| 2021/0256267 | A1 | 8/2021 | Ranasinghe et al. |
| 2021/0256835 | A1 | 8/2021 | Ranasinghe et al. |

FOREIGN PATENT DOCUMENTS

| | | | |
|---|---|---|---|
| JP | H05228122 | A | 9/1993 |
| JP | 4777640 | B2 | 9/2011 |
| WO | WO 96/15594 | A2 | 5/1996 |
| WO | WO 99/13698 | A1 | 3/1999 |
| WO | WO 00/42911 | A1 | 7/2000 |
| WO | WO 00/44274 | A2 | 8/2000 |
| WO | WO 03/007815 | | 1/2003 |
| WO | WO 03/028549 | | 4/2003 |
| WO | WO 2005/087097 | | 9/2005 |
| WO | WO 09/093159 | | 7/2009 |
| WO | WO 2009/093159 | A1 | 7/2009 |
| WO | WO 2010/014743 | | 2/2010 |

OTHER PUBLICATIONS

Jul. 10, 2020 Defendants Sotera Wireless, Inc. and Hon Hai Precision Industry Co. Ltd.'s Amended Local Patent Rule 4.1 Preliminary Claim Constructions with Extrinsic Evidence, and including Exhibits A-I, *Masimo Corporation* v. *Sotera Wireless, Inc. and Hon Hai Precision Industry Co., Ltd.*, Case No. 3:19-cv-01100-BAS-NLS, 63 pages.

Jul. 24, 2020 Masimo Corporation's Responsive Claim Constructions and Extrinsic Evidence, and including Exhibit A, *Masimo Corporation* v. *Sotera Wireless, Inc. and Hon Hai Precision Industry Co., Ltd.*, Case No. 3:19-cv-01100-BAS-NLS, 98 pages.

Jul. 24, 2020 Defendants Sotera Wireless, Inc. and Hon Hai Precision Industry Co. Ltd.'s Local Patent Rule 4.1 Preliminary Responsive Claim Constructions with Extrinsic Evidence, *Masimo Corporation* v. *Sotera Wireless, Inc. and Hon Hai Precision Industry Co., Ltd.*, Case No. 3:19-cv-01100-BAS-NLS, 11 pages.

Aug. 10, 2020 Joint Hearing Statement, and including Exhibits 1-2 and Appendices A-I, *Masimo Corporation* v. *Sotera Wireless, Inc. and Hon Hai Precision Industry Co., Ltd.*, Case No. 3:19-cv-01100-BAS-NLS, 480 pages.

Sep. 22, 2020 Plaintiff Masimo Corporation's Opening Claim Construction Brief, *Masimo Corporation* v. *Sotera Wireless, Inc. and Hon Hai Precision Industry Co., Ltd.*, Case No. 3:19-cv-01100-BAS-NLS, 33 pages.

Sep. 22, 2020 Declaration of Jack Goldberg in Support of Plaintiff Masimo Corporation's Opening Claim Construction Brief, *Masimo Corporation* v. *Sotera Wireless, Inc. and Hon Hai Precision Industry Co., Ltd.*, Case No. 3:19-cv-01100-BAS-NLS, 30 pages.

Sep. 22, 2020 Defendants Sotera Wireless, Inc. and Hon Hai Precision Industry Co., Ltd.'s Opening Markman Brief, *Masimo Corporation* v. *Sotera Wireless, Inc. and Hon Hai Precision Industry Co., Ltd.*, Case No. 3:19-cv-01100-BAS-NLS, 33 pages.

Sep. 22, 2020 Declaration of Dr. George Yanulis in Support of Defendants' Opening Claim Construction Brief, *Masimo Corporation* v. *Sotera Wireless, Inc. and Hon Hai Precision Industry Co., Ltd.*, Case No. 3:19-cv-01100-BAS-NLS, 64 pages.

Definition of "initiate", excerpt from New Oxford American Dictionary, Third Edition, 2010, 4 pages.

Definition of "initiate", excerpt from The New Oxford American Dictionary, 2001, 6 pages.

Dec. 7, 2020 Decision Granting Institution of Inter Partes Review, *Sotera Wireless, Inc.* v. *Masimo Corporation*, Inter Partes Review No. IPR2020-01078, 51 pages.

International Search Report for PCT/US2009/052146, dated Dec. 15, 2009.

International Preliminary Report on Patentability and Written Opinion for PCT/US2009/052146 dated Feb. 10, 2011.

Rheineck-Leyssius, MD, et al., "Advanced Pulse Oximeter Signal Processing Technology Compared to Simple Averaging. I. Effect on Frequency of Alarms in the Operating Room", Journal of Clinical Anesthesia, The Netherlands, May 1999, vol. 11, pp. 192-195.

Cust, AE, et al., "Alarm settings for the Marquette 8000 pulse oximeter to prevent hyperoxic and hypoxic episodes", Journal Paediatric Child Health, 1999, vol. 35, pp. 159-162.

Lawless, Stephen T., "Crying wolf: False alarms in a pediatric intensive care unit", Critical Care Medicine, 1994, vol. 22, No. 6, pp. 981-985.

Informal Expert Report of Dr. Stephen Barker, Lead Case No. 16-05968-LT11, executed Feb. 10, 2017.

Impact of Clinical Alarms On Patient Safety, ACCE Healthcare Technology Foundation, 2006, 20 pages.

Taenzer, M.D., Andreas, "Impact of Pulse Oximetry Surveillance on Rescue Events and Intensive Care Unit Transfers", The American Society of Anesthesiologists, Inc., Feb. 2010, vol. 112, No. 2, pp. 282-287.

Stefanescu, MD MSc, Beatrice, "Improved Filtering of Pulse Oximeter Monitoring Alarms in the Neonatal ICU: Bedside Significance", Respiratory Care, Jan. 2016, vol. 61, No. 1, pp. 85-89.

Rheineck-Leyssius, A.T., et al., "Influence of pulse oximeter lower alarm limit on the incidence of hypoxaemia in the recovery room", British Journal of Anaesthesia, 1997, vol. 79, pp. 460-464.

Rheineck-Leyssius, MD, Aart, et al., "Influence of Pulse Oximeter Settings on the Frequency of Alarms, and Detection of Hypoxemia", Journal of Clinical Monitoring and Computing, 1998, vol. 14, pp. 151-156.

Pan, MD., Peter, "Intraoperative Pulse Oximetry: Frequency and Distribution of Discrepant Data", Journal of Clinical Monitoring and Computing, Nov./Dec. 1994, vol. 6, pp. 491-495.

Graham, Kelly, et al., Monitor Alarm Fatigue: Standardizing Use of Physiological Monitors and Decreasing Nuisance Alarms, American Journal of Critical Care, Jan. 2010, vol. 19, No. 1, pp. 27-37.

Barker, PhD, MD, Steven, "'Motion-Resistant' Pulse Oximetry: A Comparison of New and Old Models" Department of Anesthesiology, 2002, vol. 95, pp. 967-972.

National Patient Safety Goals Effective Jan. 1, 2015, Hospital Accreditation Program, The Joint Commission, Jan. 2015, pp. 1-17.

Brostowicz, Heather, et al. Oxygen saturation monitoring in the Neonatal Intensive Care Unit (NICU): Evaluation of a new alarm management, Journal of Neonatal-Perinatal Medicine 3, 2010, pp. 135-139.

Kowalczyk, Liz, "Patient alarms often unheard, unheeded" The Boston Globe, Feb. 13, 2011, in 5 pages.

Taenzer, Andreas, et al., "Postoperative Monitoring—The Dartmouth Experience", The Official Journal of the Anesthesia Patient Safety Foundation, Spring-Summer 2012, vol. 27, No. 1, pp. 1-28.

Tobin, Martin, "Principles and Practice of Intensive Care Monitoring", 1998, in 30 pages.

Severinghaus, M.D., John, et al., Pulse Oximeter Failure Thresholds in Hypotension and Vasoconstriction, Anesthesiology, Sep. 1990, vol. 73, No. 3, pp. 532-537.

Pologe, Jonas A., "Pulse Oximetry: Technical Aspects of Machine Design", International Anesthesiology Clinics, Advances in Oxygen Monitoring, Fall, 1987, vol. 25, No. 3, pp. 137-153.

Tremper, Ph.D., Kevin et al., "Pulse Oximetry", Medical Intelligence Article, Anesthesiology, Jan. 1989, vol. 70, No. 1, pp. 98-108.

Bosque, PhD, Elena, "Symbiosis of nurse and machine through fuzzy logic: Improved specificity of a neonatal pulse oximeter alarm", Dec. 1995, vol. 18, Issue 2, pp. 67-75.

Paine, MPH, Christine, et al., "Systematic review of physiologic monitor alarm characteristics and pragmatic interventions to reduce alarm frequency" J Hosp Med., Feb. 2017, vol. 11, No. 2, pp. 136-144.

Top 10 Technology Hazards for 2012, Guidance Article, Nov. 2011, www.ecri.org, pp. 358-373.

Top 10 Technology Hazards for 2013, Health Devices, ECRI Institute, Nov. 2012, reprinted from vol. 41, Issue 11, in 25 pages.

Top 10 Health Technology Hazards for 2014, Health Devices, ECRI Institute, Nov. 2013, www.ecri.org/2014hazards, 1 page.

Masimo Advanced Alarm Performance: An Evidence-Based Approach to Reduce False Alarms and Nuisance Alarms, 2010, in 8 pages.

(56) References Cited

OTHER PUBLICATIONS

Complaint for Patent Infringement, *Masimo Corporation* v. *Sotera Wireless and Hon Hai Precision Industry Co., Ltd.,* Case No. 3:19-cv-01100-BAS-NLS, filed Jun. 12, 2019, in 385 pages.
Jun. 12, 2019 Complaint for Patent Infringement and Demand for Jury Trial, *Masimo Corporation* v. *Sotera Wireless and Hon Hai Precision Industry Co., Ltd.,* Case No. 3:19-cv-01100-BAS-NLS, 385 pages. [Uploaded in 2 parts].
Oct. 3, 2019 Defendant Sotera Wireless, Inc.'s Answer to Plaintiff's Complaint for Patent Infringement, *Masimo Corporation* v. *Sotera Wireless and Hon Hai Precision Industry Co., Ltd.,* Case No. 3:19-cv-01100-BAS-NLS, 26 pages.
Oct. 3, 2019 Defendant Hon Hai Precision Industry Co., Ltd.'s Notice of Motion and Motion Pursuant to Rule 12(b)(6) to Dismiss Plaintiff's Complaint, *Masimo Corporation* v. *Sotera Wireless and Hon Hai Precision Industry Co., Ltd.,* Case No. 3:19-cv-01100-BAS-NLS, 3 pages.
Oct. 3, 2019 Defendant Hon Hai Precision Industry Co., Ltd.'s Memorandum of Points and Authorities in Support of Motion Pursuant to Rule 12(b)(6) to Dismiss Plaintiff's Complaint, *Masimo Corporation* v. *Sotera Wireless and Hon Hai Precision Industry Co., Ltd.,* Case No. 3:19-cv-01100-BAS-NLS, 16 pages.
Oct. 24, 2019 Defendant Sotera Wireless, Inc.'s First Amended Answer to Plaintiff's Complaint for Patent Infringement and Demand for Jury Trial, *Masimo Corporation* v. *Sotera Wireless and Hon Hai Precision Industry Co., Ltd.,* Case No. 3:19-cv-01100-BAS-NLS, 32 pages.
Ferrell, "Design and Construct Miniaturized Biosensor/Transmitter System," Dept. of Physics, University of Tennessee, Jun. 1999, 77 pages.
Perng et al., "Acceleration Sensing Glove (ASG)," Berkeley Sensor & Actuator Center, University of California, Berkeley, Feb. 1999, 3 pages.
Raghunath et al., "User Interfaces for Applications on a Wrist Watch, Wearable Computing Platforms," IBM TJ Watson Research Center, New York, US, Personal Ubiquitous Computing, vol. 6, issue 1, Feb. 2002, pp. 17-30.
Stein et al., "Development of a Commercially Successful Wearable Data Collection System," Digest of Papers. Second International Symposium on Wearable Computers, Pittsburgh, PA, USA, Oct. 19-20, 1998, pp. 18-24.
Billinghurst et al., "Wearable Devices: New Ways to Manage Information," Computer, vol. 32, No. 1, Jan. 1999, pp. 57-64.
Berggren, "Wireless communication in telemedicine using Bluetooth and IEEE 802.11b," Department of Information Technology, Uppsala University, Sweden, Nov. 2001, 32 pages.
Adler, "A Cost-Effective Portable Telemedicine Kit for Use in Developing Countries," Massachusetts Institute of Technology, May 2000, 96 pages.
Satava, et al., "The Physiologic Cipher at Altitude: Telemedicine and Real-Time Monitoring of Climbers on Mount Everest," Telemedicine Journal and e-Health, vol. 6, No. 3, Feb. 2000, pp. 303-313.
Fricke et al., "Wireless Sensor Review," Arthur D. Little, Inc., Cambridge, MA, Mar. 2001, 59 pages.
Haglund, "Bluetooth Software and Hardware Development," Imperial College of Science, Technology and Medicine, University of London, Sep. 2001, 66 pages.
Bilstrup et al., "Bluetooth in Industrial Environment," IEEE International Workshop on Factory Communication Systems, Feb. 2000, 9 pages.
Shoemake, "Wi-Fi (IEEE 802.11b) and Bluetooth: Coexistence Issues and Solutions for the 2.4 GHz ISM Band," Texas Instruments, Feb. 2001, 18 pages.
Aljuaied, "Bluetooth Technology and Its Implementation in Sensing Devices," Research Office Naval Postgraduate School, Monterey, CA, Sep. 2001, 75 pages.
Seruca et al., "Enterprise Information Systems VI," Springer, Kluwer Academic Publishers, Mar. 2006, 334 pages.
Tsien, "TrendFinder: Automated Detection of Alarmable Trends," Massachusetts Institute of Technology, Apr. 2000, 240 pages.
Tsien, "Reducing False Alarms in the Intensive Care Unit: A Systematic Comparison of Four Algorithms," Proceedings of the AMIA Annual Fall Symposium, 1997, p. 894.
Myerson et al., "An Evaluation of Ventilator Monitoring Alarms," Anaesthesia and Intensive Care, vol. 14, No. 2, May 1986, pp. 174-185.
Huang, "Intelligent Alarms: Allocating Attention Among Concurrent Processes," Stanford University, Mar. 1999, 198 pages.
Mora et al., "Intelligent Patient Monitoring and Management Systems: A Review," IEEE Engineering in Medicine and Biology Magazine, vol. 12, issue 4, Dec. 1993, pp. 23-33.
Zhang et al., "Prospective Trials of Intelligent Alarm Algorithms for Patient Monitoring," Proceedings of the AMIA Symposium, 2001, p. 1068.
Malangi, "Simulation and mathematical notation of alarms unit for computer assisted resuscitation algorithm," New Jersey Institute or Technology, Digital Commons @ NJIT, These 526, Fall 2003.
Schoenberg MD et al., "Making ICU Alarms Meaningful: A Comparison of Traditional vs. Trend-Based Algorithms," Proceedings. AMIA Symposium, 1999, pp. 379-383.
Jones, "Autonomous Patient Monitoring with a Pressure Sensor Array," Carleton University, Ontario, Canada, Sep. 2006, 185 pages.
Taenzer et al., "Impact of Pulse Oximetry Surveillance on Rescue Events and Intensive Care Unit Transfers: A Before-and-After Concurrence Study," Anesthesiology—The Journal of the American Society of Anesthesiologists, Inc., vol. 112, No. 2, Feb. 2010, pp. 282-287.
Mar. 20, 2020 Defendants Sotera Wireless Inc. and Hon Hai Precision Industry Co. Ltd.'s Invalidity Contentions, *Masimo Corporation* v. *Sotera Wireless, Inc. and Hon Hai Precision Industry Co., Ltd.,* Case No. 3:19-cv-01100-BAS-NLS, 5182 pages.
Apr. 3, 2020 Masimo Corporation's Preliminary Claim Constructions and Extrinsic Evidence, *Masimo Corporation* v. *Sotera Wireless and Hon Hai Precision Industry Co., Ltd.,* Case No. 3:19-cv-01100-BAS-NLS, 13 pages.
Apr. 3, 2020 Defendants Sotera Wireless, Inc. and Hon Hai Precision Industry Co. Ltd.'s Local Patent Rule 4.1 Preliminary Claim Constructions with Extrinsic Evidence, and including Exhibits A-I, *Masimo Corporation* v. *Sotera Wireless and Hon Hai Precision Industry Co., Ltd.,* Case No. 3:19-cv-01100-BAS-NLS, 63 pages.
Jun. 8, 2020 First Amended Complaint for Patent Infringement and Demand for Jury Trial (Exhibits 1-10 comprise publicly available or previously submitted documents and are not included herein for ease of transmission), *Masimo Corporation* v. *Sotera Wireless and Hon Hai Precision Industry Co., Ltd.,* Case No. 3:19-cv-01100-BAS-NLS, 58 pages.
Jun. 22, 2020 Defendant Sotera Wireless, Inc.'s Answer to Plaintiff's First Amended Complaint for Patent Infringement and Demand for Jury Trial (Exhibits A-X comprise publicly available or previously submitted documents and are not included herein for ease of transmission), *Masimo Corporation* v. *Sotera Wireless and Hon Hai Precision Industry Co., Ltd.,* Case No. 3:19-cv-01100-BAS-NLS, 39 pages.
Rheineck-Leyssius et al., "Influence of Pulse Oximeter Lower Alarm Limit on the Incidence of Hypoxaemia in the Recovery Room," 79 British Journal of Anesthesia, 1997, pp. 460-464.
The Institute of Electrical and Electronics Engineers, Inc., "Part 11: Wireless LAN Medium Access Control (MAC) and Physical Layer (PHY) specifications: High-speed Physical Layer in the 5 GHZ Band," IEEE Std 802.11a-1999, Supplement to IEEE Std 802.11-1999, Sep. 1999, 90 pages.
Mäkivirta et al., "Alarm-Inducing Variability in Cardiac Postoperative Data and the Effects of Prealarm Delay", Journal of Clinical Monitoring, May 1994, vol. 10, No. 3, pp. 153-162.
Rheineck-Leyssius et al., "Influence of Pulse Oximeter Settings on the Frequency of Alarms and Detection of Hypoxemia", Journal of Clinical Monitoring and Computing, Apr. 1998, vol. 14, No. 3, pp. 151-156.
Petition for Inter Partes Review of U.S. Pat. No. 10,213,108, *Sotera Wireless, Inc.* v. *Masimo Corporation*, Inter Partes Review No. IPR2020-00912, dated May 7, 2020, in 113 pages.

(56) References Cited

OTHER PUBLICATIONS

Declaration of George E. Yanulis, in support of Petition for Inter Partes Review of U.S. Pat. No. 10,213,108, Ex. 1003, *Sotera Wireless, Inc.* v. *Masimo Corporation*, Inter Partes Review No. IPR2020-00912, dated May 6, 2020, in 127 pages.
Petition for Inter Partes Review of U.S. Pat. No. 9,788,735, *Sotera Wireless, Inc.* v. *Masimo Corporation*, Inter Partes Review No. IPR2020-00954, dated May 18, 2020, in 126 pages.
Declaration of George E. Yanulis, in support of Petition for Inter Partes Review of U.S. Pat. No. 9,788,735, Ex. 1003, *Sotera Wireless, Inc.* v. *Masimo Corporation*, Inter Partes Review No. IPR2020-00954, dated May 18, 2020, in 163 pages.
Petition for Inter Partes Review of U.S. Pat. No. 9,795,300, *Sotera Wireless, Inc.* v. *Masimo Corporation*, Inter Partes Review No. IPR2020-01015, dated May 29, 2020, in 109 pages.
Declaration of George E. Yanulis, in support of Petition for Inter Partes Review of U.S. Pat. No. 9,795,300, Ex. 1003, *Sotera Wireless, Inc.* v. *Masimo Corporation*, Inter Partes Review No. IPR2020-01015, dated May 28, 2020, in 156 pages.
Petition for Inter Partes Review of U.S. Pat. No. 9,872,623, *Sotera Wireless, Inc.* v. *Masimo Corporation*, Inter Partes Review No. IPR2020-01054, dated Jun. 5, 2020, in 123 pages.
Declaration of George E. Yanulis, in support of Petition for Inter Partes Review of U.S. Pat. No. 9,872,623, Ex. 1003, *Sotera Wireless, Inc.* v. *Masimo Corporation*, Inter Partes Review No. IPR2020-01054, dated Jun. 5, 2020, in 182 pages.
Petition for Inter Partes Review of U.S. Pat. No. RE47,244, *Sotera Wireless, Inc.* v. *Masimo Corporation*, Inter Partes Review No. IPR2020-00967, dated May 21, 2020, in 112 pages.
Declaration of George E. Yanulis, in support of Petition for Inter Partes Review of U.S. Pat. No. RE47,244, Ex. 1003, *Sotera Wireless, Inc.* v. *Masimo Corporation*, Inter Partes Review No. IPR2020-00967, dated May 21, 2020, in 181 pages.
Petition for Inter Partes Review of U.S. Pat. No. RE47,353, *Sotera Wireless, Inc.* v. *Masimo Corporation*, Inter Partes Review No. IPR2020-01019, dated May 29, 2020, in 111 pages.
Declaration of George E. Yanulis, in support of Petition for Inter Partes Review of U.S. Pat. No. RE47,353, Ex. 1003, *Sotera Wireless, Inc.* v. *Masimo Corporation*, Inter Partes Review No. IPR2020-01019, dated May 28, 2020, in 190 pages.
Petition for Inter Partes Review of U.S. Pat. No. RE47,249, *Sotera Wireless, Inc.* v. *Masimo Corporation*, Inter Partes Review No. IPR2020-01033, dated Jun. 3, 2020, in 111 pages.
Declaration of George E. Yanulis, in support of Petition for Inter Partes Review of U.S. Pat. No. RE47,249, Ex. 1003, *Sotera Wireless, Inc.* v. *Masimo Corporation*, Inter Partes Review No. IPR2020-01033, dated Jun. 2, 2020, in 196 pages.
Petition for Inter Partes Review of U.S. Pat. No. RE47,218, *Sotera Wireless, Inc.* v. *Masimo Corporation*, Inter Partes Review No. IPR2020-01078, dated Jun. 11, 2020, in 66 pages.
Declaration of George E. Yanulis, in support of Petition for Inter Partes Review of U.S. Pat. No. RE47,218, Ex. 1003, *Sotera Wireless, Inc.* v. *Masimo Corporation*, Inter Partes Review No. IPR2020-01078, dated Jun. 10, 2020, in 69 pages.
Petition for Inter Partes Review of U.S. Pat. No. 10,255,994, *Sotera Wireless, Inc.* v. *Masimo Corporation*, Inter Partes Review No. IPR2020-01082, dated Jun. 11, 2020, in 88 pages.
Declaration of George E. Yanulis, in support of Petition for Inter Partes Review of U.S. Pat. No. 10,255,994, Ex. 1003, *Sotera Wireless, Inc.* v. *Masimo Corporation*, Inter Partes Review No. IPR2020-01082, dated Jun. 11, 2020, in 113 pages.
Jan. 24, 2020 Masimo Corporation's Infringement Contensions, *Masimo Corporation* v. *Sotera Wireless and Hon Hai Precision Industry Co., Ltd.*, Case No. 3:19-cv-01100-BAS-NLS, 537 pages.
Sep. 8, 2020 Defendants Sotera Wireless Inc. and Hon Hai Precision Industry Co. Ltd.'s Amended LPR 3.3 Invalidity Contentions, and including Exhibits A-I, *Masimo Corporation* v. *Sotera Wireless, Inc. and Hon Hai Precision Industry Co., Ltd.*, Case No. 3:19-cv-01100-BAS-NLS, 3151 pages.
Dec. 31, 2020 Second Amended Complaint for Patent Infringement and Demand for Jury Trial (redacted public version including publicly available exhibits), *Masimo Corporation* v. *Sotera Wireless and Hon Hai Precision Industry Co., Ltd.*, Case No. 3:19-cv-01100-BAS-NLS, 725 pages. [uploaded in 5 parts].
Jan. 14, 2021 Defendant Sotera Wireless Inc.'s Answer to Plaintiff's Second Amended Complaint for Patent Infringement and Demand for Jury Trial, *Masimo Corporation* v. *Sotera Wireless and Hon Hai Precision Industry Co., Ltd.*, Case No. 3:19-cv-01100-BAS-NLS, 53 pages.
Definitions of "oximetry," "pulse oximetry," and "invasive," excerpt from Stedman's Medical Dictionary (27th ed.), 2000, 5 pages.
Definitions of "oximeter," "pulse oximeter," and "invasive," excerpt from Dorland's Illustrated Medical Dictionary (30th ed.), 2003, 5 pages.
Definition of "port," excerpt from Webster's New World College Dictionary (4th ed.), 2001, 4 pages.
Definition of "port," excerpt from Webster's II New College Dictionary, 2001, 4 pages.
Definition of "port," excerpt from Microsoft Computer Dictionary (5th ed.), 2002, 4 pages.
Jubran, "Pulse oximetry," Critical Care 1999, vol. 3, No. 2, pp. R11-R17.
Kelleher, "Pulse Oximetry," Journal of Clinical Monitoring, vol. 5, No. 1, Jan. 1989, pp. 37-62.
Westover et al., "Human Factors Analysis of an ICU," Journal of Clinical Engineering, vol. 23, No. 2, Mar./Apr. 1998, pp. 110-116.
Parati et al., "Self blood pressure monitoring at home by wrist devices: a reliable approach?" Journal of Hypertension, vol. 20, No. 4, 2002, pp. 573-578.
Hardesty, "Clothed in Health," MIT Technology Review, Jul. 1, 2001, last accessed Feb. 17, 2021, and retrieved from https://www.technologyreview.com/2001/07/01/235697/clothed-in-health, 9 pages.
Datex AS/3TM Anesthesia Monitor Operator's Manual, Jan. 1995, 399 pages. [Uploaded in 2 parts].
Gordon et al., "2012 Anthropometric Survey of U.S. Army Personnel: Methods and Summary Statistics," U.S. Army Natick Soldier Research, Dec. 2014, 454 pages.
Printouts from apple.com and Samsung.com websites showing common smartphone specifications, last accessed Feb. 18, 2021, and retrieved from https://www.apple.com/iphone/compare/?device1=iphoneX&device2=iphone11&device3=iphone12, and https://www.samsung.com/global/galaxy/compare-smartphones/, 16 pages.
Datasheet for EPROM/ROM-Based 8-bit CMOS Microcontroller Series, PIC16C5X, Microchip Technology Inc., 2013, 192 pages.
Running Armband & Wristband Phone Holder, Forearm Armband Phone Holder, 360° Rotatable Armband for iPhone Samsung Galaxy Google Pixel, Cellphone Wristband Great for Hiking Biking Running, Amazon.com, printed May 12, 2021, and retrieved from https://www.amazon.com/Running-Armband-Wristband-Rotatable-Cellphone/dp/B08DJ2B6X5/, 2 pages.
Registration Interface—Selection and General Information, AT&T Co. Standard, Bell System Practices, Section 463-400-100, Issue 1, May 1978, 5 pages.
Registration Interface—Adapter Arrangements RJA1X, RJA2X, and RJA3X, AT&T Co. Standard, Bell System Practices, Section 463-400-100, Issue 2, May 1979, 6 pages.
Modular Connector Guide, C2G, printed May 12, 2021, and retrieved from https://www.cablestogo.com/learning/connector-guides/modular, 3 pages.
IEEE Standard for a High Performance Serial Bus—Amendment 1, IEEE Std 1394a-2000 (Amendment to IEEE Std 1394-1995), The Institute of Electrical and Electronics Engineers, Inc., Mar. 30, 2000, 204 pages.
Kästle et al., "A New Family of Sensors for Pulse Oximetry," Hewlett-Packard Journal, Article 7, Feb. 1997, pp. 1-17.
Portzon Set of 2 Neoprene Dumbbell Hand Weights, Anti-Slip, Anti-roll, Amazon.com, printed Feb. 22, 2021, and retrieved from https://www.amazon.com/Neoprene-Dumbbell-Weights-Anti-slip-Anti-roll/dp/B088M26WRH/, 9 pages.
JG Webster, ed., Design of Pulse Oximeter, Medical Science Series, IOP Publishing Ltd, 1997, 256 pages. [Uploaded in 4 parts].

(56) References Cited

OTHER PUBLICATIONS

Invicta Men's Pro Diver Scuba Quartz Chronograph Carbon Fiber Bezel Abalone Dial Bracelet Watch, 50mm, Amazon.com, printed May 17, 2021, and retrieved from https://www.amazon.com/Invicta-Quartz-Chronograph-Abalone-Bracelet/dp/B0772D8BWK/, 6 pages.
Data sheet for iKey Rugged Wearable Keyboard, Product Code AK-39, last accessed Jun. 17, 2021, and retrieved from https://www.ikey.com/document//?route=product/pdf&product_id=46, 2 pages.
Anderson, The Importance of Thomas Edison, Lucent Books, Inc., 1994, pp. 30-33.
Jun. 11, 2020 Sotera Wireless, Inc.'s Power of Attorney, *Sotera Wireless, Inc.* v. *Masimo Corporation*, Inter Partes Review No. IPR2020-01078, in 3 pages.
Jun. 16, 2020 Notice of Filing Date Accorded to Petition, *Sotera Wireless, Inc.* v. *Masimo Corporation*, Inter Partes Review No. IPR2020-01078, in 6 pages.
Jul. 2, 2020 Patent Owner Submission of Mandatory Notice Information, *Sotera Wireless, Inc.* v. *Masimo Corporation*, Inter Partes Review No. IPR2020-01078, in 6 pages.
Sep. 16, 2020 Patent Owner Preliminary Response, *Sotera Wireless, Inc.* v. *Masimo Corporation*, Inter Partes Review No. IPR2020-01078, in 49 pages.
Oct. 7, 2020 Order—Conduct of the Proceeding, *Sotera Wireless, Inc.* v. *Masimo Corporation*, Inter Partes Review No. IPR2020-01078, 3 pages.
Oct. 7, 2020 Notice of Decision in Related Judicial Matter, *Sotera Wireless, Inc.* v. *Masimo Corporation*, Inter Partes Review No. IPR2020-01078, in 3 pages.
Oct. 7, 2020 Patent Owner Updated Exhibit List, *Sotera Wireless, Inc.* v. *Masimo Corporation*, Inter Partes Review No. IPR2020-01078, in 4 pages.
Oct. 16, 2020 Petitioner's Reply to Preliminary Response, *Sotera Wireless, Inc.* v. *Masimo Corporation*, Inter Partes Review No. IPR2020-01078, in 12 pages.
Oct. 23, 2020 Patent Owner Sur-Reply re Fintiv Factors, *Sotera Wireless, Inc.* v. *Masimo Corporation*, Inter Partes Review No. IPR2020-01078, in 11 pages.
Dec. 7, 2020 Decision Granting Institution of Inter Partes Review, *Sotera Wireless, Inc.* v. *Masimo Corporation*, Inter Partes Review No. IPR2020-01078, in 51 pages.
Dec. 7, 2020 Scheduling Order, *Sotera Wireless, Inc.* v. *Masimo Corporation*, Inter Partes Review No. IPR2020-01078, in 11 pages.
Dec. 21, 2020 Patent Owner Objections to Evidence, *Sotera Wireless, Inc.* v. *Masimo Corporation*, Inter Partes Review No. IPR2020-01078, 7 pages.
Jan. 26, 2021 Sotera's Updated Mandatory Notices, *Sotera Wireless, Inc.* v. *Masimo Corporation*, Inter Partes Review No. IPR2020-01078, in 4 pages.
Jan. 28, 2021 Masimo's Notice of Deposition of George Yanulis, *Sotera Wireless, Inc.* v. *Masimo Corporation*, Inter Partes Review No. IPR2020-01078, in 3 pages.
Feb. 1, 2021 Sotera_s Updated Power of Attorney, *Sotera Wireless, Inc.* v. *Masimo Corporation*, Inter Partes Review No. IPR2020-01078, in 3 pages.
Feb. 2, 2021 Masimo's Unopposed Motion for DCK to Appear Pro Hac Vice, *Sotera Wireless, Inc.* v. *Masimo Corporation*, Inter Partes Review No. IPR2020-01078, in 7 pages.
Feb. 4, 2021 Order Granting Masimo's Unopposed Motion for DCK to Appear Pro Hac Vice, *Sotera Wireless, Inc.* v. *Masimo Corporation*, Inter Partes Review No. IPR2020-01078, in 4 pages.
Feb. 9, 2021 Masimo's Updated Mandatory Notice Information Adding Back-Up Counsel, *Sotera Wireless, Inc.* v. *Masimo Corporation*, Inter Partes Review No. IPR2020-01078, in 6 pages.
Feb. 9, 2021 Masimo's Supplemental Power of Attorney Adding DCK, *Sotera Wireless, Inc.* v. *Masimo Corporation*, Inter Partes Review No. IPR2020-01078, in 3 pages.
Mar. 5, 2021 Masimo's Updated Mandatory Notice Information Adding Back-Up Counsel, *Sotera Wireless, Inc.* v. *Masimo Corporation*, Inter Partes Review No. IPR2020-01078, in 6 pages.
Mar. 5, 2021 Patent Owner Response, *Sotera Wireless, Inc.* v. *Masimo Corporation*, Inter Partes Review No. IPR2020-01078, in 69 pages.
Mar. 29, 2021 Sotera's Notice of Deposition of Jack Goldberg, *Sotera Wireless, Inc.* v. *Masimo Corporation*, Inter Partes Review No. IPR2020-01078, in 4 pages.
May 28, 2021 Sotera's Reply, *Sotera Wireless, Inc.* v. *Masimo Corporation*, Inter Partes Review No. IPR2020-01078, in 28 pages.
Jun. 8, 2021 Masimo's Objections to Evidence, *Sotera Wireless, Inc.* v. *Masimo Corporation*, Inter Partes Review No. IPR2020-01078, in 5 pages.
Jul. 9, 2021 Patent Owner Sur-Reply, *Sotera Wireless, Inc.* v. *Masimo Corporation*, Inter Partes Review No. IPR2020-01078, in 30 pages.
Jul. 30, 2021 Sotera's Request for Oral Argument, *Sotera Wireless, Inc.* v. *Masimo Corporation*, Inter Partes Review No. IPR2020-01078, in 4 pages.
Jul. 30, 2021 Masimo's Request for Oral Argument, *Sotera Wireless, Inc.* v. *Masimo Corporation*, Inter Partes Review No. IPR2020-01078, in 4 pages.
Aug. 3, 2021 Order Setting Oral Argument for Sep. 24, 2021, *Sotera Wireless, Inc.* v. *Masimo Corporation*, Inter Partes Review No. IPR2020-01078, in 9 pages.
Aug. 20, 2021 Order Re-Setting Oral Argument for Sep. 24, 2021 at 2pm, *Sotera Wireless, Inc.* v. *Masimo Corporation*, Inter Partes Review No. IPR2020-01078, in 5 pages.
Sep. 16, 2021 Masimo's Demonstratives for Oral Argument, *Sotera Wireless, Inc.* v. *Masimo Corporation*, Inter Partes Review No. IPR2020-01078, in 59 pages.
Sep. 16, 2021 Sotera;s Oral Hearing Demonstratives, *Sotera Wireless, Inc.* v. *Masimo Corporation*, Inter Partes Review No. IPR2020-01078, in 40 pages.
Sep. 20, 2021 Petitioner's Notice re Demonstratives for Oral Argument, *Sotera Wireless, Inc.* v. *Masimo Corporation*, Inter Partes Review No. IPR2020-01078, in 43 pages.
Sep. 20, 2021 Patent Owner Updated Exhibit List, *Sotera Wireless, Inc.* v. *Masimo Corporation*, Inter Partes Review No. IPR2020-01078, in 4 pages.
Masimo Opposition to Sotera Motion to Stay Proceedings, *Sotera Wireless, Inc.* v. *Masimo Corporation*, Inter Partes Review No. IPR2020-01078, Exhibit 2001, in 22 pages.
Case Management Order, *Sotera Wireless, Inc.* v. *Masimo Corporation*, Inter Partes Review No. IPR2020-01078, Exhibit 2002, in 8 pages.
Order Granting Joint Motion to Modify Case Management Order, *Sotera Wireless, Inc.* v. *Masimo Corporation*, Inter Partes Review No. IPR2020-01078, Exhibit 2003, in 3 pages.
Mar. 20, 2020 Defendants' Invalidity Contentions, *Sotera Wireless, Inc.* v. *Masimo Corporation*, Inter Partes Review No. IPR2020-01078, Exhibit 2004, in 38 pages.
Sep. 8, 2020 Defendants' Amended Invalidity Contentions, *Sotera Wireless, Inc.* v. *Masimo Corporation*, Inter Partes Review No. IPR2020-01078, Exhibit 2007, in 43 pages.
Joint Hearing Statement, *Sotera Wireless, Inc.* v. *Masimo Corporation*, Inter Partes Review No. IPR2020-01078, Exhibit 2008, in 23 pages.
Oct. 6, 2020 Order Granting in Part Joint Motion to Modify Case Management Order, *Sotera Wireless, Inc.* v. *Masimo Corporation*, Inter Partes Review No. IPR2020-01078, Exhibit 2009, in 4 pages.
DCK Declaration ISO PHV Motion, *Sotera Wireless, Inc.* v. *Masimo Corporation*, Inter Partes Review No. IPR2020-01078, Exhibit 2010, in 4 pages.
Declaration of Jack Goldberg, *Sotera Wireless, Inc.* v. *Masimo Corporation*, Inter Partes Review No. IPR2020-01078, Exhibit 2011, in 52 pages.
Oxford Dictionary of English (2010)—Threshold, *Sotera Wireless, Inc.* v. *Masimo Corporation*, Inter Partes Review No. IPR2020-01078, Exhibit 2012, in 3 pages.
American Heritage Dictionary (2011)—Threshold, *Sotera Wireless, Inc.* v. *Masimo Corporation*, Inter Partes Review No. IPR2020-01078, Exhibit 2013, in 3 pages.

(56) References Cited

OTHER PUBLICATIONS

Yanulis Transcript, Feb. 10, 2021 vol. 6, *Sotera Wireless, Inc.* v. *Masimo Corporation*, Inter Partes Review No. IPR2020-01078, Exhibit 2014, in 223 pages.
Jack Goldberg CV Feb. 22, 2021, *Sotera Wireless, Inc.* v. *Masimo Corporation*, Inter Partes Review No. IPR2020-01078, Exhibit 2015, in 21 pages.
Patent Owner Demonstratives, *Sotera Wireless, Inc.* v. *Masimo Corporation*, Inter Partes Review No. IPR2020-01078, Exhibit 2016, in 59 pages.
Prosecution History of RE47,218, *Sotera Wireless, Inc.* v. *Masimo Corporation*, Inter Partes Review No. IPR2020-01078, Exhibit 1002, in 310 pages, uploaded in 2 parts.
Declaration of George E. Yanulis, *Sotera Wireless, Inc.* v. *Masimo Corporation*, Inter Partes Review No. IPR2020-01078, Exhibit 1003, in 69 pages.
CV of George E. Yanulis, *Sotera Wireless, Inc.* v. *Masimo Corporation*, Inter Partes Review No. IPR2020-01078, Exhibit 1004, in 8 pages.
Masimo's Complaint for Patent Infringement (*Masimo* v. *Sotera*, 19cv01100), *Sotera Wireless, Inc.* v. *Masimo Corporation*, Inter Partes Review No. IPR2020-01078, Exhibit 1008, in 44 pages.
Service of Summons and Complaint upon Sotera (*Masimo* v. *Sotera*, 19cv01100), *Sotera Wireless, Inc.* v. *Masimo Corporation*, Inter Partes Review No. IPR2020-01078, Exhibit 1009, in 4 pages.
RE218 Prosecution History Excerpt, Application with Preliminary Amendment, *Sotera Wireless, Inc.* v. *Masimo Corporation*, Inter Partes Review No. IPR2020-01078, Exhibit 1010, in 55 pages.
RE218 Prosecution History Excerpt, Non-Final Office Action, *Sotera Wireless, Inc.* v. *Masimo Corporation*, Inter Partes Review No. IPR2020-01078, Exhibit 1011, in 45 pages.
RE218 Prosecution History Excerpt, Amendment and Response to Office Action, *Sotera Wireless, Inc.* v. *Masimo Corporation*, Inter Partes Review No. IPR2020-01078, Exhibit 1012, in 10 pages.
RE218 Prosecution History Excerpt, Notice of Allowance, *Sotera Wireless, Inc.* v. *Masimo Corporation*, Inter Partes Review No. IPR2020-01078, Exhibit 1013, in 14 pages.
'570 Prosecution History Excerpt, Notice of Allowance, *Sotera Wireless, Inc.* v. *Masimo Corporation*, Inter Partes Review No. IPR2020-01078, Exhibit 1015, in 49 pages.
Masimo Corporation's Infringement Contentions with Exhibit D (*Masimo* v. *Sotera*, 19cv0), *Sotera Wireless, Inc.* v. *Masimo Corporation*, Inter Partes Review No. IPR2020-01078, Exhibit 1016, in 36 pages.
Masimo's Trade Secret Complaint against Sotera in Orange County, CA, Superior Court, *Sotera Wireless, Inc.* v. *Masimo Corporation*, Inter Partes Review No. IPR2020-01078, Exhibit 1017, in 20 pages.
Oral Ruling in Prior Trade Secret Litigation, *Sotera Wireless, Inc.* v. *Masimo Corporation*, Inter Partes Review No. IPR2020-01078, Exhibit 1018, in 1 page.
Final Order in Prior Trade Secret Litigation, *Sotera Wireless, Inc.* v. *Masimo Corporation*, Inter Partes Review No. IPR2020-01078, Exhibit 1019, in 117 pages.
Sotera Motion to Stay, *Sotera Wireless, Inc.* v. *Masimo Corporation*, Inter Partes Review No. IPR2020-01078, Exhibit 1036, in 29 pages.
Order Vacating Claim Construction Hearing, *Sotera Wireless, Inc.* v. *Masimo Corporation*, Inter Partes Review No. IPR2020-01078, Exhibit 1037, in 1 page.
Defendants' Stipulation of Invalidity Contentions, *Sotera Wireless, Inc.* v. *Masimo Corporation*, Inter Partes Review No. IPR2020-01078, Exhibit 1038, in 10 pages.
Declaration of Bryan Bergeron ISO Sotera's Reply to Petition, *Sotera Wireless, Inc.* v. *Masimo Corporation*, Inter Partes Review No. IPR2020-01078, Exhibit 1040, in 35 pages.
Bryan Bergeron CV, *Sotera Wireless, Inc.* v. *Masimo Corporation*, Inter Partes Review No. IPR2020-01078, Exhibit 1041, in 40 pages.
Apr. 22, 2021 Deposition Transcript of Jack Goldberg, *Sotera Wireless, Inc.* v. *Masimo Corporation*, Inter Partes Review No. IPR2020-01078, Exhibit 1042, in 106 pages.
Macmillan English Dictionary, *Sotera Wireless, Inc.* v. *Masimo Corporation*, Inter Partes Review No. IPR2020-01078, Exhibit 1043, in 3 pages.
Nov. 29, 2021, Judgment Final Written Decision Determining All Challenged Claims Unpatentable, *Sotera Wireless, Inc.* v. *Masimo Corporation*, Inter Partes Review No. IPR2020-01078, 77 pages.
Jan. 25, 2022 Patent Owner's Notice of Appeal to the U.S. Court of Appeals for the Federal Circuit, *Sotera Wireless, Inc.* v. *Masimo Corporation*, Inter Partes Review No. IPR2020-01078, 83 pages.
US 9,579,050, 02/2017, Al-Ali (withdrawn).
US 8,845,543, Diab et al. (withdrawn).
Coetzee, et al., "Noise-Resistant Pulse Oximetry Using a Synthetic Reference Signal," IEEE Transactions on Biomedical Engineering, IEEE Service Center, Piscataway, NJ, vol. 47, No. 8, dated Aug. 1, 2000.
Invitation to Pay Additional Fees document, including communication relating to the results of a partial Search Report issued in related application No. PCT/US2011/026545, dated Jun. 22, 2011, in 5 pages.
"Propaq Encore Vital Signs Monitor: Reference Guide," Welch Allyn, Inc., 2009 in 144 pages.

* cited by examiner

ADAPTIVE ALARM SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

PRIORITY CLAIM TO RELATED PROVISIONAL APPLICATIONS

[The present applicantion] *This is a reissue continuation application, meaning it is a reissue of U.S. Pat. No. 9,775,570, and is also a continuation of U.S. Reissue patent application Ser. No. 16/184,908, which is reissue of U.S. Pat. No. 9,775,570 and a continuing reissue of U.S. Reissue patent application Ser. No. 15/881,602, which is a reissue of U.S. Pat. No. 9,775,570, issued on Oct. 3, 2017 and titled "Adaptive Alarm System," which is a continuation of U.S. patent application Ser. No. 13/037,184, filed Feb. 18, 2011 titled Adaptive Alarm System, which* claims priority benefit under 35 U.S.C. § 119(e) to [U.S. patent application Ser. No. 13/037,184 filed Feb. 18, 2011 titled Adaptive Alarm System;]Provisional Patent Application Ser. No. 61/309,419, filed Mar. 1, 2010 titled Adaptive Threshold Alarm System; and U.S. Provisional Patent Application Ser. No. 61/328,630, filed Apr. 27, 2010 titled Adaptive Alarm Systems; *more than one reissue application has been filed for the reissue of U.S. Pat. No. 9,775,570, including U.S. patent application Ser. No. 16/800,971 (the present application), U.S. patent application Ser. No. 16/184,908 and U.S. patent application Ser. No. 15/881,602;* all of the above-cited provisional patent applications are hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

SUMMARY OF THE INVENTION

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, Soffouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Masimo Laboratories, Irvine, Calif (Masimo Labs) and all incorporated by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced physiological parameter measurement systems have also gained rapid acceptance in a wide variety of medical applications, including surgical wards, intensive care and neonatal units, general wards, home care, physical training, and virtually all types of monitoring scenarios.

FIGS. 1-3 illustrate problems and issues associated with physiological parameter measurement systems having fixed threshold alarm schemas. FIG. 1 illustrates a lower-limit, fixed-threshold alarm schema with respect to an oxygen saturation ($SpO_2$) parameter. Two alarm thresholds, $D_L$ (delay) and $ND_L$ (no delay), are defined. If oxygen saturation falls below $D_L$ for a time delay greater than TD, an alarm is triggered. If oxygen saturation falls below $ND_L$ an alarm is immediately triggered. $D_L$ 120 is typically set around or somewhat above 90% oxygen saturation and $ND_L$ 130 is typically set at 5% to 10% below $D_L$. For example, say a person's oxygen saturation 110 drops below $D_L$ 120 at $t=t_1$ 162 and stays below $D_L$ for at least a time delay TD 163. This triggers a delayed alarm 140 at $t=t_2$ 164, where $t_2=t_1+$ TD. The alarm 140 remains active until oxygen saturation 110 rises above $D_L$ 120 at $t=t_3$ 166. As another example, say that oxygen saturation 110 then drops below $ND_L$ 130, which triggers an immediate alarm 150 at t=t4 168. The alarm 150 remains active until oxygen saturation 110 rises above $D_L$ 120 at $t=t_5$ 169.

FIG. 2 illustrates an upper-limit, fixed-threshold alarm schema with respect to an oxygen saturation ($SpO_2$) parameter. This alarm scenario is particularly applicable to the avoidance of ROP (retinopathy of prematurity). Again, two alarm thresholds, $D_U$ (delay) and $ND_U$ (no delay), are defined. $D_U$ 220 might be set at or around 85% oxygen saturation and $ND_U$ 230 might be set at or around 90% oxygen saturation. For example, a neonate's oxygen saturation 210 rises above $D_U$ 220 at $t=t_1$ 262 and stays above $D_U$ for at least a time delay TD 263. This triggers a delayed alarm 240 at $t=t_2$ 264, where $t_2=t_1+$TD. The alarm 240 remains active until oxygen saturation 210 falls below $D_U$ 220 at $t=t_3$ 166. Oxygen saturation 210 then rises above $ND_U$ 230, which triggers an immediate alarm 250 at $t=t_4$ 268. The alarm 250 remains active until oxygen saturation 210 falls below $D_U$ 220 at $t=t_5$ 269.

FIG. 3 illustrates a baseline drift problem with the fixed threshold alarm schema described above. A person's oxygen saturation is plotted on an oxygen saturation ($SpO_2$) versus time graph 300. In particular, during a first time interval $T_1$ 362, a person has an oxygen saturation 310 with a relatively stable "baseline" 312 punctuated by a shallow, transient desaturation event 314. This scenario may occur after the person has been on oxygen so that baseline oxygen saturation is near 100%. Accordingly, with a fixed threshold alarm 330 set at, say, 90%, the transient event 314 does not trigger a nuisance alarm. However, the effects of oxygen treatments wear off over time and oxygen saturation levels drift downward 350. In particular, during a second time interval $T_2$ 364, a person has an oxygen saturation 320 with a relatively stable baseline 322. The later baseline 322 is established at a substantially lower oxygen saturation than the earlier baseline 312. In this scenario, a shallow, transient desaturation event 324 now exceeds the alarm threshold 330 and results in a nuisance alarm. After many such nuisance alarms, a caregiver may lower the alarm threshold 330 to unsafe levels or turn off alarms altogether, significantly hampering the effectiveness of monitoring oxygen saturation.

A fixed threshold alarm schema is described above with respect to an oxygen saturation parameter, such as derived from a pulse oximeter. However, problematic fixed threshold alarm behavior may be exhibited in a variety of parameter measurement systems that calculate physiological parameters related to circulatory, respiratory, neurological, gastrointestinal, urinary, immune, musculoskeletal, endocrine or reproductive systems, such as the circulatory and respiratory parameters cited above, as but a few examples.

An adaptive alarm system, as described in detail below, advantageously provides an adaptive threshold alarm to solve false alarm and missed true alarm problems associated with baseline drift among other issues. For example, for a lower limit embodiment, an adaptive alarm system adjusts an alarm threshold downwards when a parameter baseline is established at lower values. Likewise, for an upper limit embodiment, the adaptive alarm system adjusts an alarm threshold upwards in accordance with baseline drift so as to avoid nuisance alarms. In an embodiment, the rate of baseline movement is limited so as to avoid masking of transients. In an embodiment, the baseline is established along upper or lower portions of a parameter envelop so as to provide a margin of safety in lower limit or upper limit systems, respectively.

One aspect of an adaptive alarm system is responsive to a physiological parameter so as to generate an alarm threshold that adapts to baseline drift in the parameter and reduce false alarms without a corresponding increase in missed true alarms. The adaptive alarm system has a parameter derived from a physiological measurement system using a sensor in communication with a living being. A baseline processor calculates a parameter baseline from an average value of the parameter. Parameter limits specify an allowable range of the parameter. An adaptive threshold processor calculates an adaptive threshold from the parameter baseline and the parameter limits. An alarm generator is responsive to the parameter and the adaptive threshold so as to trigger an alarm indicative of the parameter crossing the adaptive threshold. The adaptive threshold is responsive to the parameter baseline so as to increase in value as the parameter baseline drifts to a higher parameter value and to decrease in value as the parameter baseline drifts to a lower parameter value.

In various embodiments, the baseline processor has a sliding window that identifies a time slice of parameter values. A trend calculator determines a trend from an average of the parameter values in the time slice. A response limiter tracks only the relatively long-term transitions of the trend. A bias calculator deletes the highest parameter values in the time slice or the lowest parameter values in the time slice so as to adjust the baseline to either a lower value or a higher value, respectively. The adaptive threshold becomes less response to baseline drift as the baseline approaches a predefined parameter limit. A first adaptive threshold is responsive to lower parameter limits and a second adaptive threshold is responsive to upper parameter limits. The alarm generator is responsive to both positive and negative transients from the baseline according to the first adaptive threshold and the second adaptive threshold. The first adaptive threshold is increasingly responsive to negative transients and the second adaptive threshold is decreasingly responsive to positive transients as the baseline trends toward lower parameter values.

Another aspect of an adaptive alarm system measures a physiological parameter, establishes a baseline for the parameter, adjusts an alarm threshold according to drift of the baseline and triggers an alarm in response to the parameter measurement crossing the alarm threshold. In various embodiments, the baseline is established by biasing a segment of the parameter, calculating a biased trend from the biased segment and restricting the transient response of the biased trend. The alarm threshold is adjusted by setting a parameter limit and calculating a delta difference between the alarm threshold and the baseline as a linear function of the baseline according to the parameter limit. The delta difference is calculated by decreasing delta as the baseline drifts toward the parameter limit and increasing delta as the baseline drifts away from the parameter limit. A parameter limit is set by selecting a first parameter limit in relation to a delayed alarm and selecting a second parameter limit in relation to an un-delayed alarm. A segment of the parameter is biased by windowing the parameter measurements, removing a lower value portion of the windowed parameter measurements and averaging a remaining portion of the windowed parameter measurements. An upper delta difference between an upper alarm threshold and the baseline is calculated and a lower delta difference between a lower alarm threshold and the baseline is calculated.

A further aspect of an adaptive alarm system has a baseline processor that inputs a parameter and outputs a baseline according to a trend of the parameter. An adaptive threshold processor establishes an alarm threshold at a delta difference from the baseline. An alarm generator triggers an alarm based upon a parameter transient from the baseline crossing the alarm threshold. In various embodiments, a trend calculator outputs a biased trend and the baseline is responsive to the biased trend so as to reduce the size of a transient that triggers the alarm. A response limiter reduces baseline movement due to parameter transients. The adaptive threshold processor establishes a lower alarm threshold below the baseline and an upper alarm threshold above the baseline so that the alarm generator is responsive to both positive and negative transients from the baseline. The baseline processor establishes a lower baseline biased above the parameter trend and an upper baseline biased below the parameter trend. The lower alarm threshold is increasingly responsive to negative transients and the upper alarm threshold is decreasingly responsive to positive transients as the baseline trends toward lower parameter values.

DETAILED DESCRIPTION OF THE PREFERRED EMBODIMENTS

Figure 1:
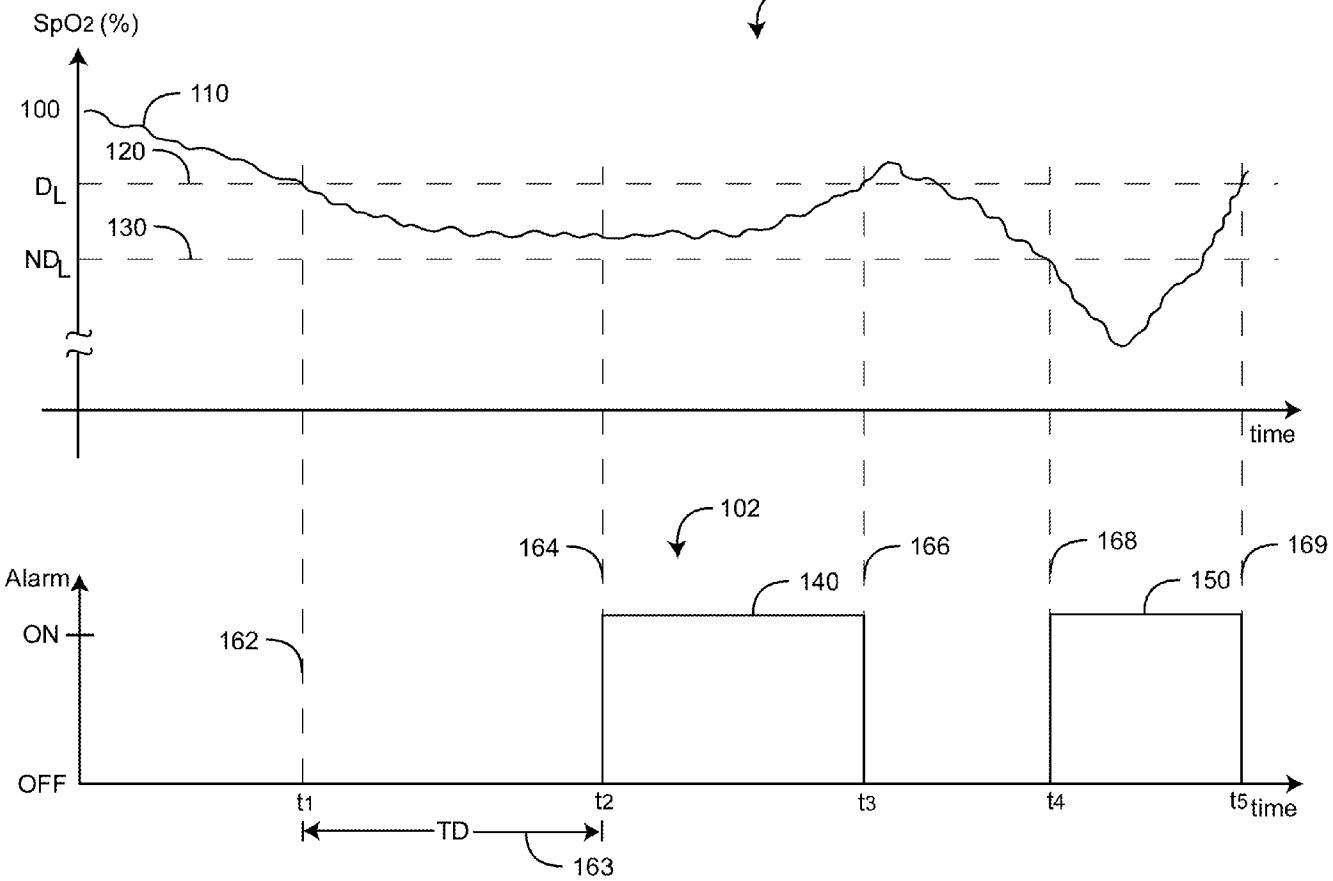
FIGS. 1-3 are exemplar graphs illustrating problems and issues associated with physiological parameter measurement systems having fixed threshold alarm schemas.
Figure 2:
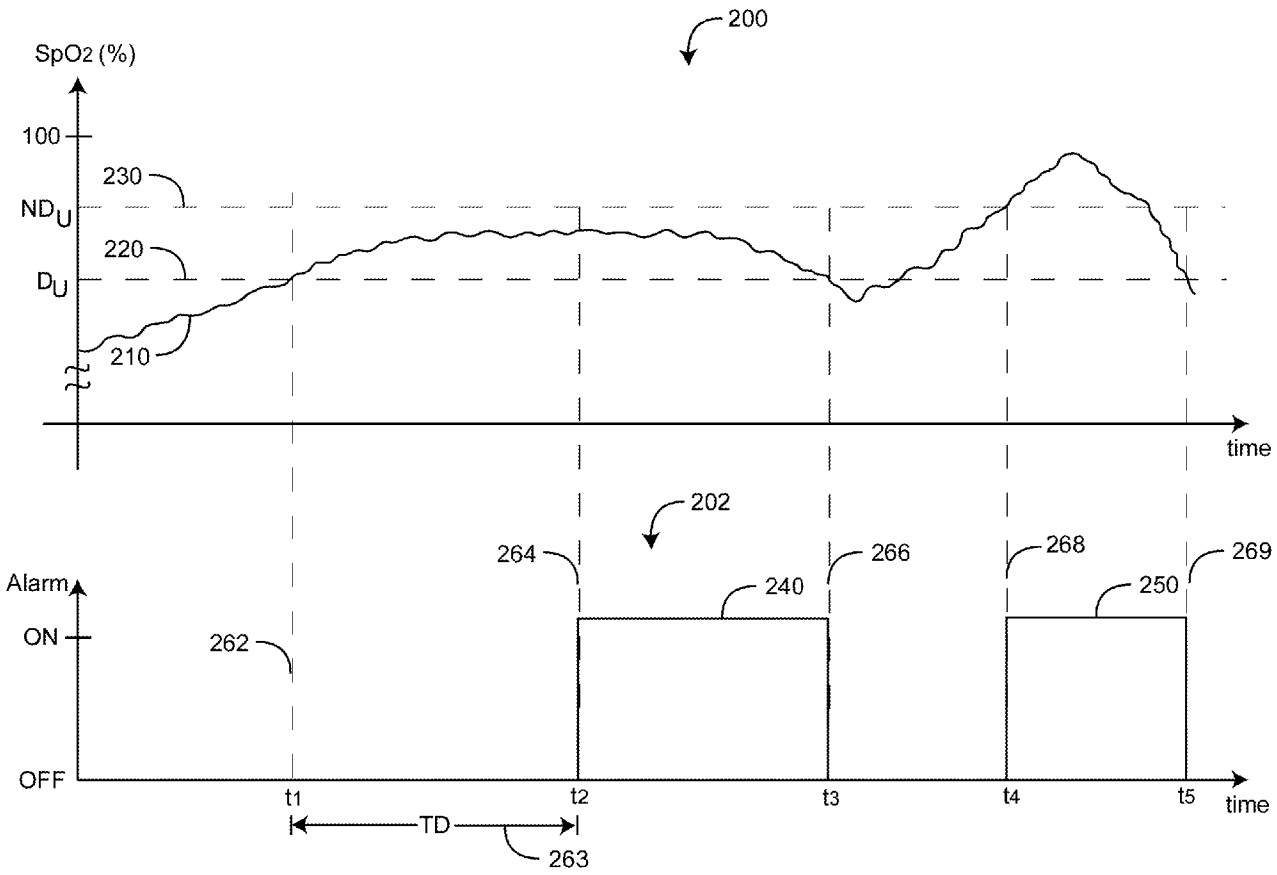
Figure 3:
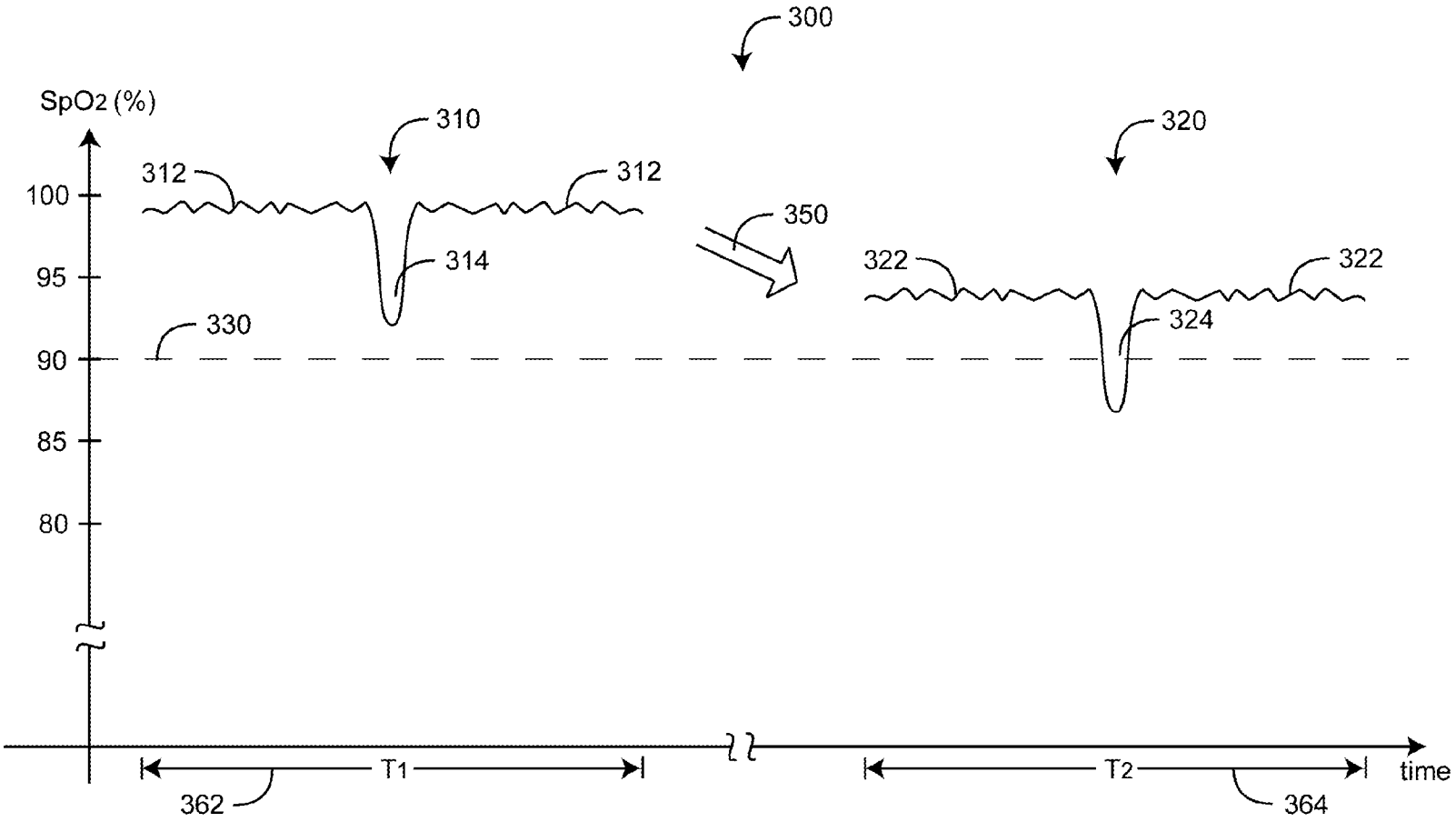
Figure 4A:
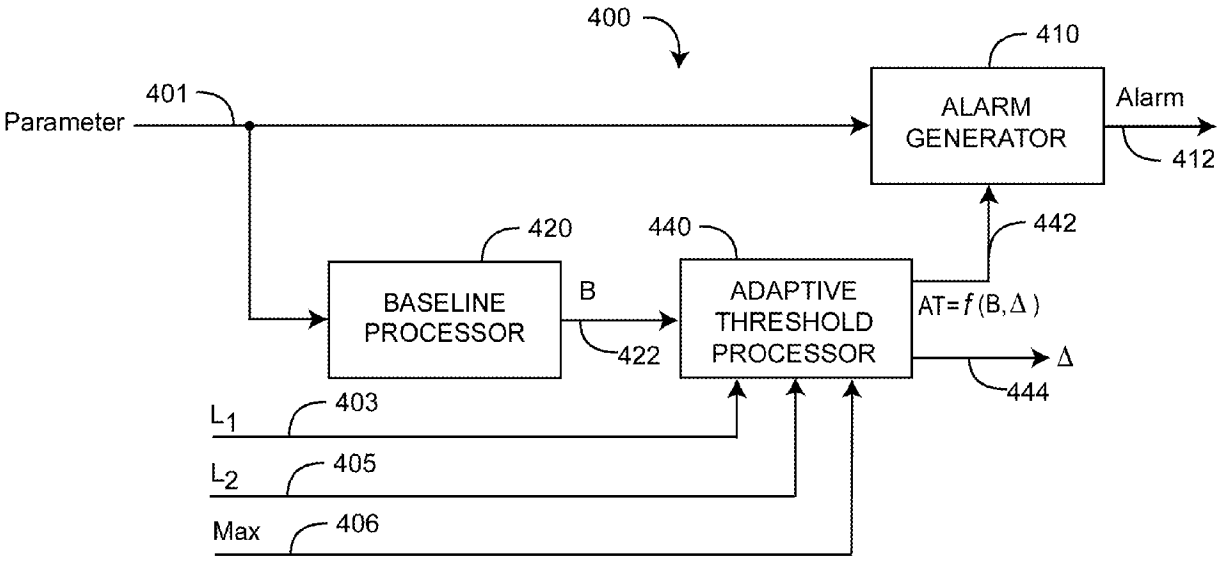
FIGS. 4A-B are general block diagrams of an adaptive alarm system having lower parameter limits.
Figure 4B:
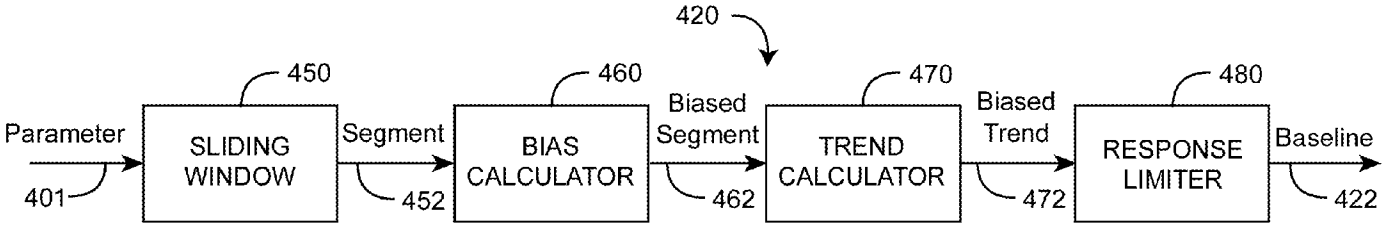

FIGS. 4A-B illustrate an adaptive alarm system 400 embodiment having lower parameter limits $L_1$ and $L_2$. As shown in FIG. 4A, the adaptive alarm system 400 has parameter 401, first limit ($L_1$) 403, second limit ($L_2$) 405 and maximum parameter value (Max) 406 inputs and generates a corresponding alarm 412 output. The parameter 401 input is generated by a physiological parameter processor, such as a pulse oximeter or an advanced blood parameter processor described above, as examples. The adaptive alarm system 400 has an alarm generator 410, a baseline processor 420, and an adaptive threshold processor 440. The alarm generator 410 has parameter 401 and adaptive threshold (AT) 442 inputs and generates the alarm 412 output accordingly. A baseline processor 420 has the parameter 401 input and generates a parameter baseline (B) 422 output. The baseline processor 420, is described in detail with respect to FIG. 4B, below. An adaptive threshold processor 440 has parameter baseline (B) 422, $L_1$ 403, $L_2$ 405 and Max 406 inputs and generates the adaptive threshold (AT) 442. The adaptive threshold processor 440 is described in detail with respect to FIGS. 5A-B, below.

As shown in FIG. 4A, in an embodiment $L_1$ 403 and $L_2$ 405 may correspond to conventional fixed alarm thresholds with and without an alarm time delay, respectively. For an adaptive threshold schema, however, $L_1$ 403 and $L_2$ 405 do not determine an alarm threshold per se, but are reference levels for determining an adaptive threshold (AT) 442. In an embodiment, $L_1$ 403 is an upper limit of the adaptive alarm threshold AT when the baseline is near the maximum parameter value (Max), and $L_2$ 405 is a lower limit of the adaptive alarm threshold, as described in detail with respect to FIGS. 5A-B, below. In an exemplar embodiment when the parameter is oxygen saturation, $L_1$ 403 is set at or around 90% and $L_2$ 405 is set at 5 to 10% below $L_1$, i.e. at 85% to 80% oxygen saturation. Many other $L_1$ and $L_2$ values may be used for an adaptive threshold schema as described herein.

Also shown in FIG. 4A, in an embodiment the alarm 412 output is triggered when the parameter 401 input falls below AT 442 and ends when the parameter 401 input rises above AT 442 or is otherwise cancelled. In an embodiment, the alarm 412 output is triggered after a time delay (TD), which may be fixed or variable. In an embodiment, the time delay (TD) is a function of the adaptive threshold (AT) 442. In an embodiment, the time delay (TD) is zero when the adaptive threshold (AT) is at the second lower limit ($L_2$) 405.

As shown in FIG. 4B, a baseline processor 420 embodiment has a sliding window 450, a bias calculator 460, a trend calculator 470 and a response limiter 480. The sliding window 450 inputs the parameter 401 and outputs a time segment 452 of the parameter 401. In an embodiment, each window incorporates a five minute span of parameter values. The bias calculator 460 advantageously provides an upward shift in the baseline (B) 422 for an additional margin of error over missed true alarms. That is, a baseline 422 is generated that tracks a higher-than-average range of parameter values, effectively raising the adaptive threshold AT slightly above a threshold calculated based upon a true parameter average, as shown and described in detail with respect to FIGS. 7-8, below. In an embodiment, the bias calculator 460 rejects a lower range of parameter values from each time segment 452 from the sliding window so as to generate a biased time segment 462.

Also shown in FIG. 4B, the trend calculator 470 outputs a biased trend 472 of the remaining higher range of parameter values in each biased segment 462. In an embodiment, the biased trend 462 is an average of the values in the biased time segment 462. In other embodiments, the biased trend 462 is a median or mode of the values in the biased time segment 462. The response limiter 480 advantageously limits the extent to which the baseline 422 output tracks the biased trend 472. Accordingly, the baseline 422 tracks only relatively longer-lived transitions of the parameter, but does not track (and hence mask) physiologically significant parameter events, such as oxygen desaturations for a $SpO_2$ parameter to name but one example. In an embodiment, the response limiter 480 has a low pass transfer function. In an embodiment, the response limiter 480 is a slew rate limiter.

Figure 5B:
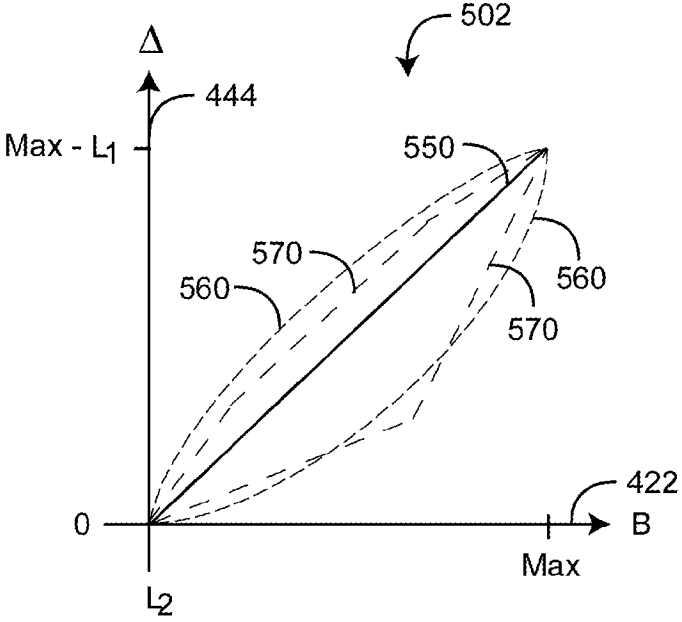
FIGS. 5A-B are a graph of a physiological parameter versus delta space and a graph of delta versus baseline, respectively, illustrating the relationship between a baseline, a lower-limit adaptive threshold and a variable difference delta between the baseline and the adaptive threshold.
Figure 5A:
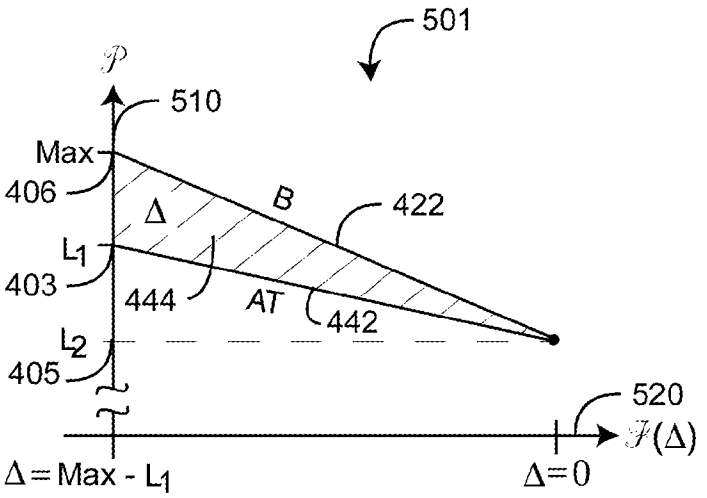

FIGS. 5A-B further illustrate an adaptive threshold processor 440 (FIG. 4A) having a baseline (B) 422 input and generating an adaptive threshold (AT) 442 output and a delta (Δ) 444 ancillary output according to parameter limits $L_1$ 403, $L_2$ 405 and Max 406, as described above. As shown in FIG. 5A, as the baseline (B) 422 decreases (increases) the adaptive threshold (AT) 444 monotonically decreases (increases) between $L_1$ 403 and $L_2$ 405. Further, as the baseline (B) 422 decreases (increases) the delta (Δ) 444 difference between the baseline (B) 422 and the adaptive threshold (AT) 442 monotonically decreases (increases) between Max−$L_1$ and zero.

As shown in FIG. 5B, the relationship between the delta (Δ) 444 and the baseline (B) 444 may be linear 550 (solid line), non-linear 560 (small-dash lines) or piecewise-linear (large-dash lines), to name a few. In an embodiment, the adaptive threshold processor 440 (FIG. 4A) calculates an adaptive threshold (AT) 442 output in response to the baseline (B) 422 input according to a linear relationship. In a linear embodiment, the adaptive threshold processor 440 (FIG. 4A) calculates the adaptive threshold (AT) 442 according to EQS. 1-2:

$$\Delta = -\left(\frac{\text{Max} - L_1}{\text{Max} - L_2}\right)(\text{Max} - B) + (\text{Max} - L_1) \tag{1}$$

$$AT = B - \Delta \tag{2}$$

where Δ=Max−$L_1$ @ B=Max; Δ=0 @ B=$L_2$
and where AT=$L_1$ @ B=Max; AT=$L_2$ @ B=$L_2$, accordingly.

Figure 6:
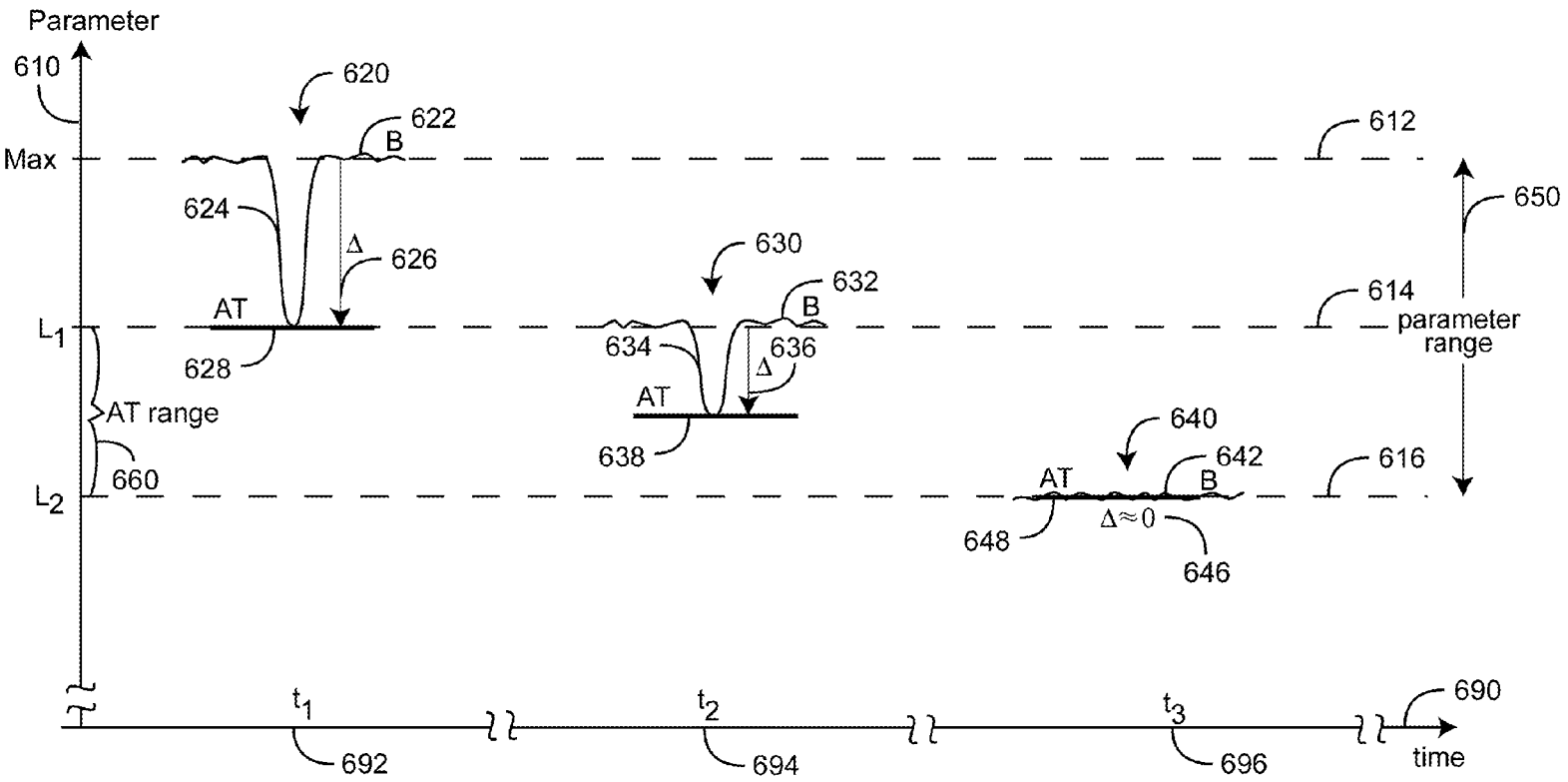
FIG. 6 is an exemplar graph of a physiological parameter versus time illustrating an adaptive alarm system having a lower-limit adaptive threshold.

FIG. 6 illustrates the operational characteristics an adaptive alarm system 400 (FIG. 4A) having parameter limits Max 612, $L_1$ 614 and $L_2$ 616 and an alarm responsive to a baseline (B) 622, 632, 642; an adaptive threshold (AT) 628, 638, 648; and a corresponding Δ 626, 636, 646 according to EQS. 1-2, above. In particular, a physiological parameter 610 is graphed versus time 690 for various time segments $t_1$, $t_2$, $t_3$ 692-696. The parameter range (PR) 650 is:

$$PR = \text{Max} - L_2 \tag{3}$$

and the adaptive threshold range (ATR) 660 is:

$$ATR = L_1 - L_2 \tag{4}$$

As shown in FIG. 6, during a first time period $t_1$ 692, a parameter segment 620 has a baseline (B) 622 at about Max 612. As such, Δ 626=Max−$L_1$ and the adaptive threshold (AT) 628 is at about $L_1$ 614. Accordingly, a transient 624 having a size less than Δ 626 does not trigger the alarm 412 (FIG. 4A).

Also shown in FIG. 6, during a second time period $t_2$ 694, a parameter segment 630 has a baseline (B) 632 at about $L_1$ 614. As such, Δ 636 is less than Max−$L_1$ and the adaptive threshold (AT) 638 is between $L_1$ and $L_2$. Accordingly, a smaller transient 634 will trigger the alarm as compared to a transient 624 in the first time segment.

Further shown in FIG. 6, during a third time period $t_3$ 696, a parameter segment 640 has a baseline (B) 642 at about $L_2$ 616. As such, Δ 646 is about zero and the adaptive threshold (AT) 648 is at about $L_2$. Accordingly, even a small negative transient will trigger the alarm. As such, the behavior of the alarm threshold AT 628, 638, 648 advantageously adapts to higher or lower baseline values so as to increase or decrease the size of negative transients that trigger or do not trigger the alarm 412 (FIG. 4A).

Figure 7:
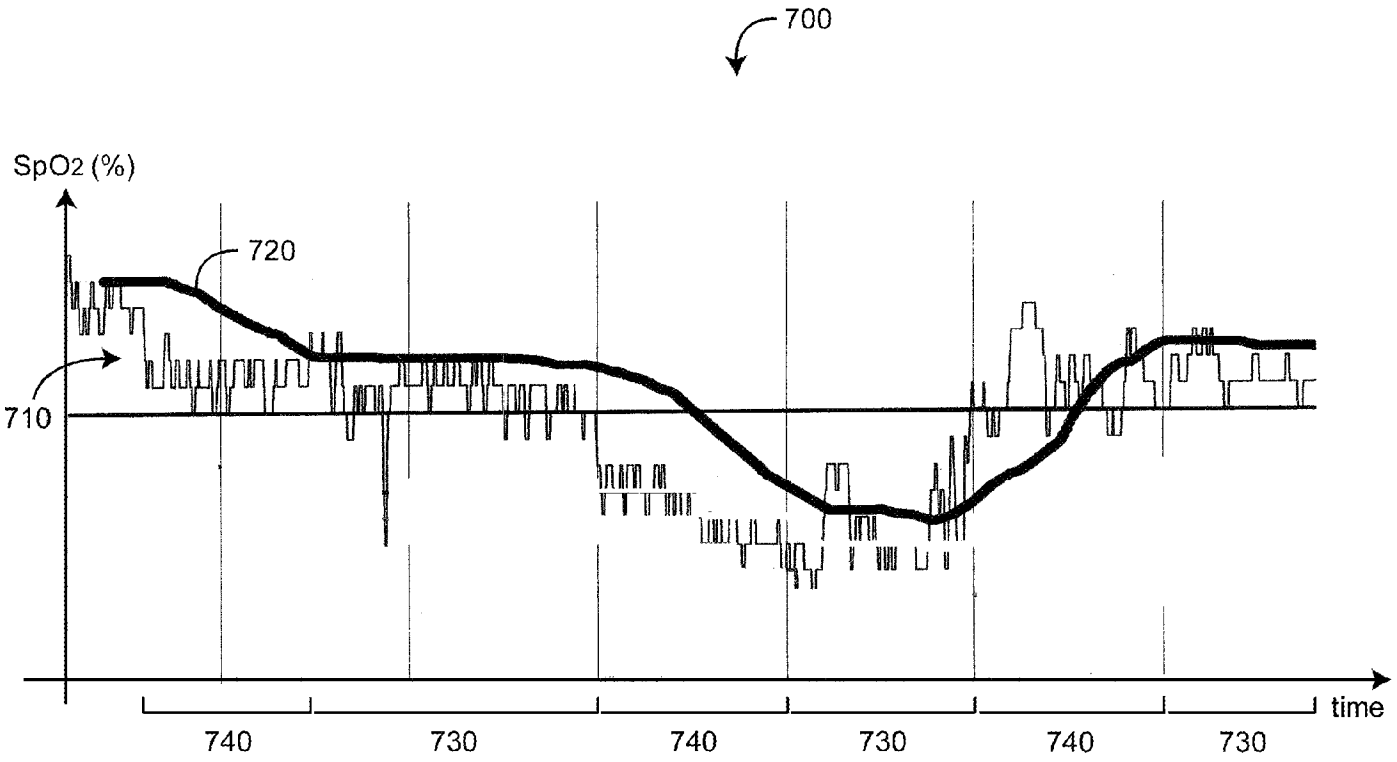
FIG. 7 is a graph of oxygen saturation versus time illustrating a baseline for determining an adaptive threshold.

FIG. 7 is a parameter versus time graph 700 illustrating the characteristics of an adaptive alarm system 400 (FIGS. 4A-B), as described with respect to FIGS. 4-6, above, where the parameter is oxygen saturation ($SpO_2$). The graph 700 has a $SpO_2$ trace 710 and a superimposed baseline trace 720. The graph 700 also delineates tracking periods 730, where the baseline 720 follows the upper portions of $SpO_2$ values, and lagging periods 740, where the baseline 720 does not follow transient $SpO_2$ events. The tracking time periods 730 illustrate that the baseline 720 advantageously tracks at the higher range of $SpO_2$ values 710 during relatively stable (flat) periods, as described above. Lagging time periods 740 illustrate that the baseline 720 is advantageously limited in response to transient desaturation events so that significant desaturations fall below an adaptive threshold (not shown) and trigger an alarm accordingly.

Figure 8:
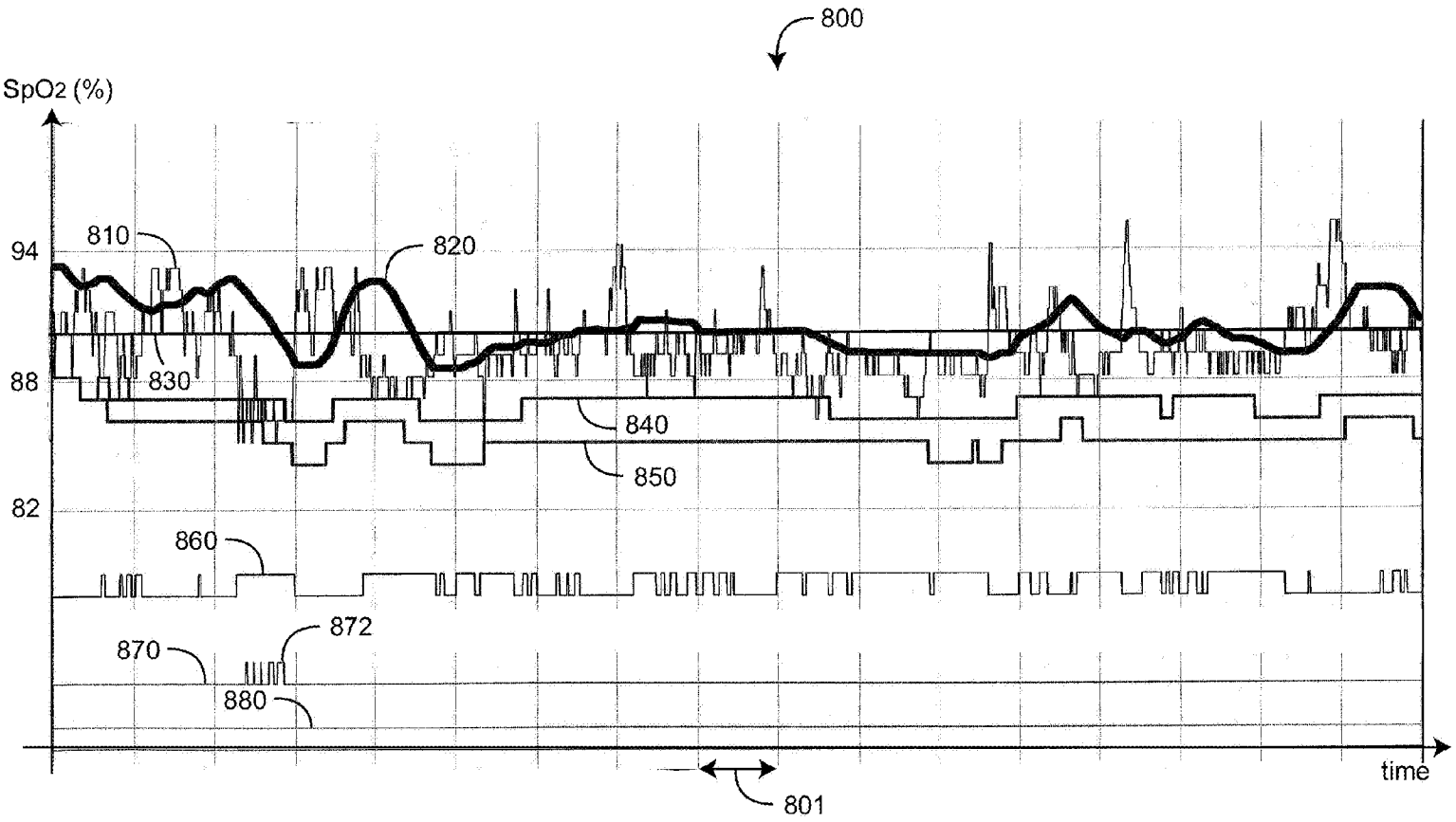
FIG. 8 is a graph of oxygen saturation versus time comparing adaptive-threshold alarm performance with fixed-threshold alarm performance.

FIG. 8 is a parameter versus time graph 800 illustrating characteristics of an adaptive alarm system 400 (FIGS. 4A-B), as described with respect to FIGS. 4-6, above, where the parameter is oxygen saturation ($SpO_2$). Vertical axis ($SpO_2$) resolution is 1%. The time interval 801 between vertical hash marks is five minutes. The graph 800 has a $SpO_2$ trace 810 and a baseline trace 820. The graph 800 also has a fixed threshold trace 830, a first adaptive threshold (AT) trace 840 and a second AT trace 850. The graph 800 further has a fixed threshold alarm trace 860, a first adaptive threshold alarm trace 870 and a second adaptive threshold alarm trace 880. In this example, $L_1$ is 90% and $L_2$ is 85% for the first AT trace 840 and first AT alarm trace 870. $L_2$ is 80% for a second AT trace 850 and a second AT alarm trace 880. The fixed threshold 830 results in many nuisance alarms 860. By comparison, the adaptive threshold alarm with $L_2$=85% has just one time interval of alarms 872 during a roughly 6% desaturation period (from 92% to 86%). The adaptive threshold alarm with $L_2$=80%, has no alarms during the 1 hour 25 minute monitoring period.

Figure 9A:
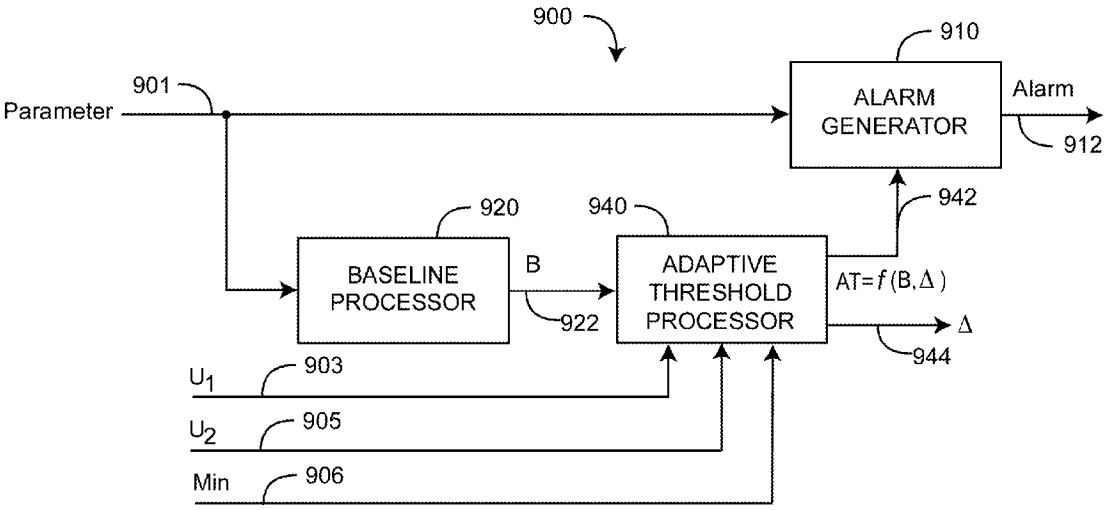
FIGS. 9A-B are general block diagrams of an adaptive alarm system having upper parameter limits.
Figure 9B:
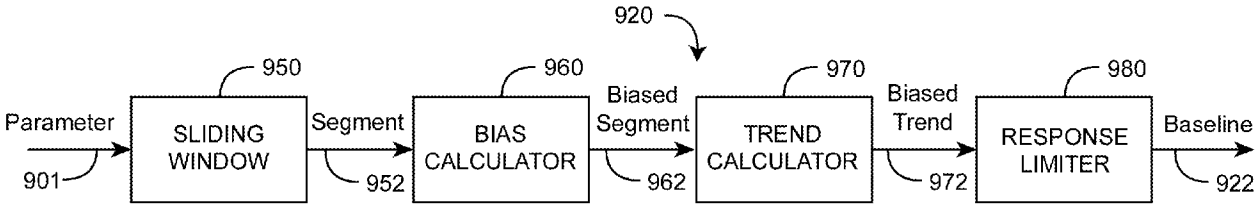

FIGS. 9A-B illustrate an adaptive alarm system 900 embodiment having upper parameter limits $U_1$ and $U_2$. As shown in FIG. 9A, the adaptive alarm system 900 has parameter 901, first limit ($U_1$) 903, second limit ($U_2$) 905 and minimum parameter value (Min) 906 inputs and generates a corresponding alarm 912 output. The parameter 901 input is generated by a physiological parameter processor, such as a pulse oximeter or an advanced blood parameter processor described above, as examples. The adaptive alarm system 900 has an alarm generator 910, a baseline processor 920, and an adaptive threshold processor 940. The alarm generator 910 has parameter 901 and adaptive threshold (AT) 942 inputs and generates the alarm 912 output accordingly. A baseline processor 920 has the parameter 901 input and generates a parameter baseline (B) 922 output. The baseline processor 920, is described in detail with respect to FIG. 9B, below. An adaptive threshold processor 940 has parameter baseline (B) 922, $U_1$ 903, $U_2$ 905 and Min 906 inputs and generates the adaptive threshold (AT) 942. The adaptive threshold processor 940 is described in detail with respect to FIGS. 10A-B, below.

As shown in FIG. 9A, in an embodiment $U_1$ 903 and $U_2$ 905 may correspond to conventional fixed alarm thresholds with and without an alarm time delay, respectively. For an adaptive threshold schema, however, $U_1$ 903 and $U_2$ 905 do not determine an alarm threshold per se, but are reference levels for determining an adaptive threshold (AT) 942. In an embodiment, $U_1$ 903 is a lower limit of the adaptive alarm threshold AT when the baseline is near the minimum parameter value (Min), and $U_2$ 905 is an upper limit of the adaptive alarm threshold, as described in detail with respect to FIGS. 10A-B, below. In an exemplar embodiment when the parameter is oxygen saturation, $U_1$ 903 is set at or around 85% and $U_2$ 905 is set at or around 90% oxygen saturation. Many other $U_1$ and $U_2$ values may be used for an adaptive threshold schema as described herein.

Also shown in FIG. 9A, in an embodiment the alarm 912 output is triggered when the parameter 901 input rises above AT 942 and ends when the parameter 901 input falls below AT 942 or is otherwise cancelled. In an embodiment, the alarm 912 output is triggered after a time delay (TD), which may be fixed or variable. In an embodiment, the time delay (TD) is a function of the adaptive threshold (AT) 942. In an embodiment, the time delay (TD) is zero when the adaptive threshold (AT) is at the second upper limit ($U_2$) 905.

As shown in FIG. 9B, a baseline processor 920 embodiment has a sliding window 950, a bias calculator 960, a trend calculator 970 and a response limiter 980. The sliding window 950 inputs the parameter 901 and outputs a time segment 952 of the parameter 901. In an embodiment, each window incorporates a five minute span of parameter values. The bias calculator 960 advantageously provides a downward shift in the baseline (B) 922 for an additional margin of error over missed true alarms. That is, a baseline 922 is generated that tracks a lower-than-average range of parameter values, effectively lowering the adaptive threshold AT slightly below a threshold calculated based upon a true parameter average. In an embodiment, the bias calculator 960 rejects an upper range of parameter values from each time segment 952 from the sliding window so as to generate a biased time segment 962.

Also shown in FIG. 9B, the trend calculator 970 outputs a biased trend 972 of the remaining lower range of parameter values in each biased segment 962. In an embodiment, the biased trend 962 is an average of the values in the biased time segment 962. In other embodiments, the biased trend 962 is a median or mode of the values in the biased time segment 962. The response limiter 980 advantageously limits the extent to which the baseline 922 output tracks the biased trend 972. Accordingly, the baseline 922 tracks only relatively longer-lived transitions of the parameter, but does not track (and hence mask) physiologically significant parameter events, such as oxygen desaturations for a $SpO_2$ parameter to name but one example. In an embodiment, the response limiter 980 has a low pass transfer function. In an embodiment, the response limiter 980 is a slew rate limiter.

Figure 10B:
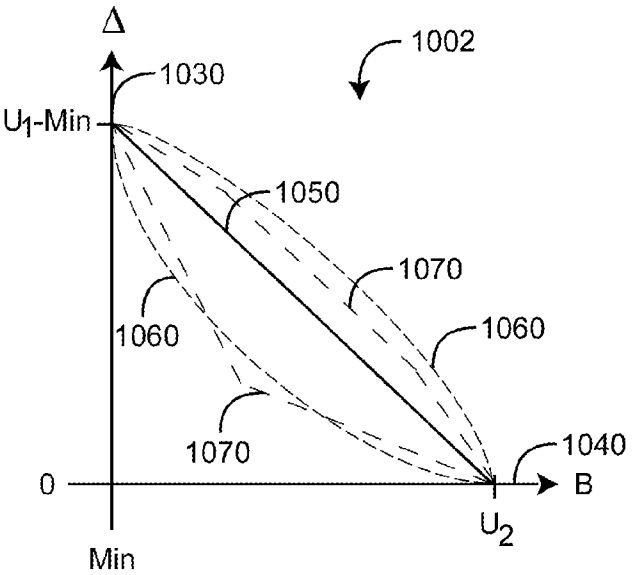
FIGS. 10A-B are a graph of a physiological parameter versus delta space and a graph of delta versus baseline, respectively, illustrating the relationship between a baseline, an upper-limit adaptive threshold and a variable delta difference between the baseline and the adaptive threshold.
Figure 10A:
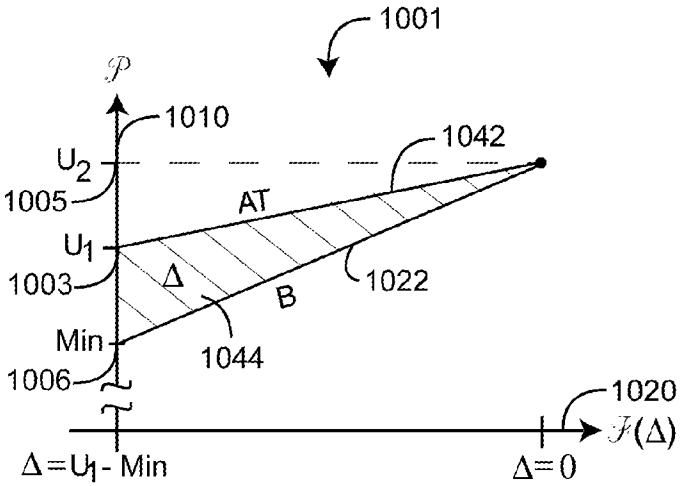

FIGS. 10A-B further illustrate an adaptive threshold processor 940 (FIG. 9A) having a baseline (B) 922 input and generating an adaptive threshold (AT) 942 output and a delta (Δ) 944 ancillary output according to parameter limits $U_1$ 903, $U_2$ 905 and Min 906, as described above. As shown in FIG. 10A, as the baseline (B) 922 decreases (increases) the adaptive threshold (AT) 944 monotonically decreases (increases) between $U_1$ 903 and $U_2$ 905. Further, as the baseline (B) 922 decreases (increases) the delta (Δ) 944 difference between the baseline (B) 922 and the adaptive threshold (AT) 942 monotonically decreases (increases) between Min−$U_1$ and zero.

As shown in FIG. 10B, the relationship between the delta (Δ) 944 and the baseline (B) 944 may be linear 550 (solid line), non-linear 560 (small-dash lines) or piecewise-linear (large-dash lines), to name a few. In an embodiment, the adaptive threshold processor 940 (FIG. 9A) calculates an adaptive threshold (AT) 942 output in response to the baseline (B) 922 input according to a linear relationship. In a linear embodiment, the adaptive threshold processor 940 (FIG. 9A) calculates the adaptive threshold (AT) 942 according to EQS. 5-6:

$$\Delta = -\left(\frac{U_1 - \text{Min}}{U_2 - \text{Min}}\right)(B - \text{Min}) + (U_1 - \text{Min}) \tag{5}$$

$$AT = B + \Delta \tag{6}$$

where $\Delta = U_1 - \text{Min}$ @ B=Min; $\Delta = 0$ @ $B = U_2$
and where $AT = U_1$ @ B=Min; $AT = U_2$ @ $B = U_2$, accordingly.

Figure 11:
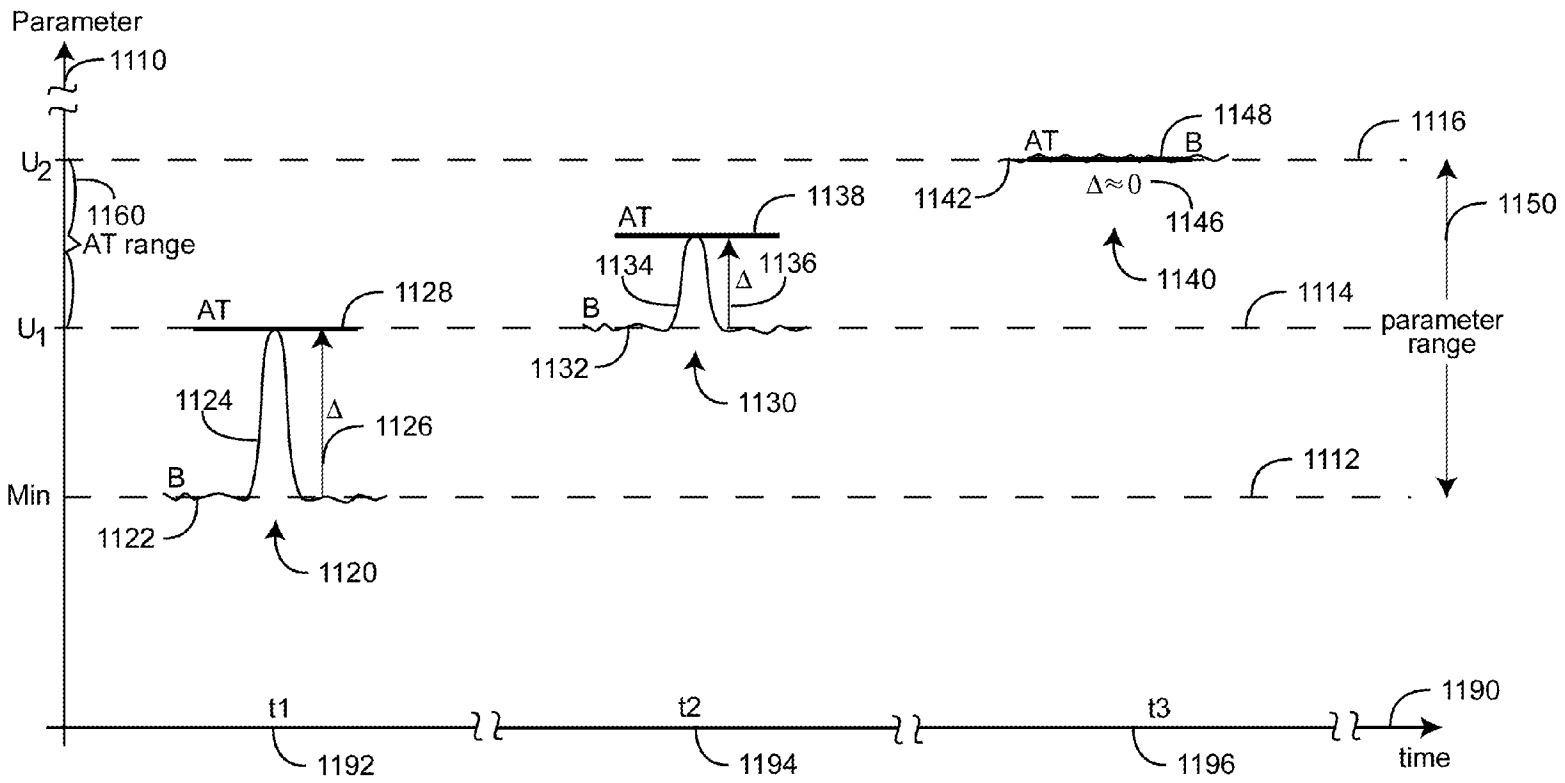
FIG. 11 is an exemplar graph of a physiological parameter versus time illustrating an adaptive alarm system having an upper-limit adaptive threshold.

FIG. 11 illustrates the operational characteristics an adaptive alarm system 900 (FIG. 9A) having parameter limits Min 1112, $U_1$ 1114 and $U_2$ 1116 and an alarm responsive to a baseline (B) 1122, 1132, 1142; an adaptive threshold (AT) 1128, 1138, 1148; and a corresponding Δ 1126, 1136, 1146 according to EQS. 5-6, above. In particular, a physiological parameter 1110 is graphed versus time 1190 for various time segments $t_1$, $t_2$, $t_3$ 1192-1196. The parameter range (PR) 1150 is:

$$PR = U_2 - \text{Min} \tag{7}$$

and the adaptive threshold range (ATR) 1160 is:

$$ATR = U_2 - U_1 \tag{8}$$

As shown in FIG. 11, during a first time period $t_1$ 1192, a parameter segment 1120 has a baseline (B) 1122 at about Min 1112. As such, Δ 1126=$U_1$−Min and the adaptive threshold (AT) 1128 is at about $U_1$ 1114. Accordingly, a transient 1124 having a size less than Δ 1126 does not trigger the alarm 912 (FIG. 9A).

Also shown in FIG. 11, during a second time period $t_2$ 1194, a parameter segment 1130 has a baseline (B) 1132 at about $U_1$ 1114. As such, Δ 1136 is less than $U_1$−Min and the adaptive threshold (AT) 1138 is between $U_1$ and $U_2$. Accordingly, a smaller transient 1134 will trigger the alarm as compared to a transient 1124 in the first time segment.

Further shown in FIG. 11, during a third time period $t_3$ 1196, a parameter segment 1140 has a baseline (B) 1142 at about $U_2$ 1116. As such, Δ 1146 is about zero and the adaptive threshold (AT) 1148 is at about $U_2$. Accordingly, even a small positive transient will trigger the alarm. As such, the behavior of the alarm threshold AT 1128, 1138, 1148 advantageously adapts to higher or lower baseline values so as to increase or decrease the size of positive transients that trigger or do not trigger the alarm 912 (FIG. 9A).

Figure 12A:
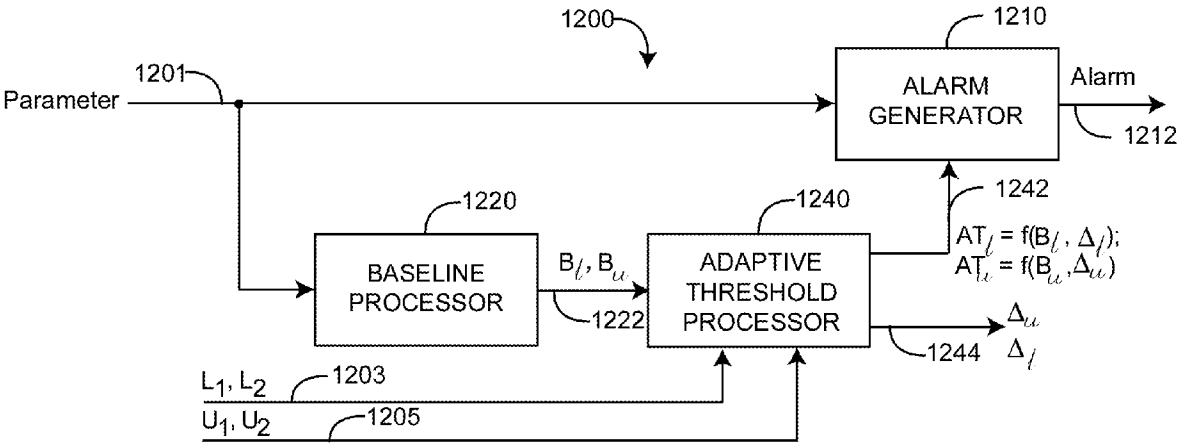
FIGS. 12A-B are general block diagrams of an adaptive alarm system having both lower alarm limits and upper alarm limits.
Figure 12B:
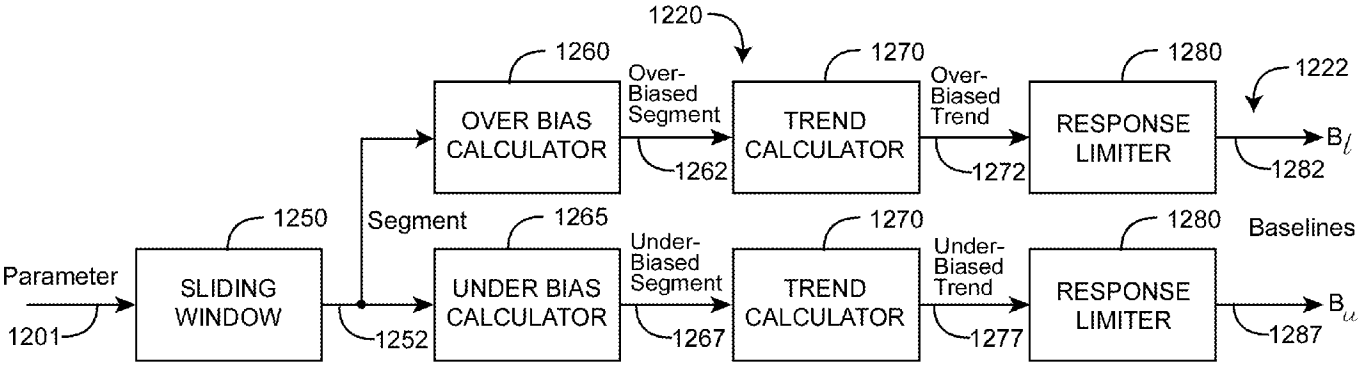

FIGS. 12A-B illustrate an adaptive alarm system 1200 embodiment having lower limits $L_1$, $L_2$ 1203, such as described with respect to FIGS. 4A-B above, or upper limits $U_1$, $U_2$ 1205 such as described with respect to FIGS. 9A-B above, or both. As shown in FIG. 12A, the adaptive alarm system 1200 has parameter 1201, lower limit 1203 and upper limit 1205 inputs and generates a corresponding alarm 1212 output. The parameter 1201 input is generated by a physiological parameter processor, such as a pulse oximeter or an advanced blood parameter processor described above, as examples. The adaptive alarm system 1200 has an alarm generator 1210, a baseline processor 1220 and an adaptive threshold processor 1240. The alarm generator 1210 has parameter 1201 and adaptive threshold (AT) 1242 inputs and generates the alarm 1212 output accordingly. A baseline processor 1220 has the parameter 1201 input and generates one or more parameter baseline 1222 outputs. The baseline processor 1220, is described in detail with respect to FIG. 12B, below. An adaptive threshold processor 1240 has parameter baseline 1222, lower limit $L_1$, $L_2$ 1203 and upper limit $U_1$, $U_2$ 1205 inputs and generates lower and upper adaptive threshold $AT_l$, $AT_u$ 1242 outputs. The adaptive threshold processor 1240 also generates ancillary upper and lower delta 1244 outputs. The adaptive threshold processor 1240 is described in detail with respect to FIGS. 13A-E, below.

As shown in FIG. 12A, in an embodiment $L_1$, $L_2$ 1203 and $U_1$, $U_2$ 1205 may correspond to conventional fixed alarm thresholds with an alarm delay ($L_1$, $U_1$) and without an alarm delay ($L_2$, $U_2$). For an adaptive threshold schema, however, these limits 1203, 1205 do not determine an alarm threshold per se, but are reference levels for determining lower and upper adaptive thresholds $AT_l$, $AT_u$ 1242.

Also shown in FIG. 12A, in an embodiment the alarm 1212 output is triggered when the parameter 1201 input falls below $AT_l$ 1242 and ends when the parameter 1201 input rises above $AT_l$ 1242 or the alarm is otherwise cancelled. Further, the alarm 1212 output is triggered when the parameter 1201 input rises above $AT_u$ 1242 and ends when the parameter 1201 input falls below $AT_u$ 1242 or the alarm is otherwise cancelled. In an embodiment, the alarm 1212 output is triggered after a time delay (TD), which may be fixed or variable. In an embodiment, the time delay (TD) is a function of the adaptive thresholds ($AT_l$, $AT_u$) 1242. In an embodiment, the time delay (TD) is zero when the lower adaptive threshold ($AT_l$) 1242 is at the second lower limit ($L_2$) 1203 or when the upper adaptive alarm threshold $AT_u$ 1242 is at the second upper limit ($U_2$) 1205.

As shown in FIG. 12B, a baseline processor 1220 embodiment has a sliding window 1250, an over-bias calculator 1260, an under-bias calculator 1265, trend calculators 1270 and response limiters 1280. The sliding window 1250 inputs the parameter 1201 and outputs a time segment 1252 of the parameter 1201. In an embodiment, each window incorporates a five minute span of parameter 1201 values.

Also shown in FIG. 12B, the over-bias calculator 1260 advantageously provides an upward shift in the lower baseline ($B_l$) 1282 for an additional margin of error over missed lower true alarms. That is, a lower baseline ($B_l$) 1282 is generated that tracks a higher-than-average range of parameter values, effectively raising the lower adaptive threshold $AT_l$ slightly above a threshold calculated based upon a true parameter average. In an embodiment, the over-bias calculator 1260 rejects a lower range of parameter values from each time segment 1252 of the sliding window 1250 so as to generate an over-biased time segment 1262.

Further shown in FIG. 12B, the under-bias calculator 1265 advantageously provides a downward shift in the upper baseline ($B_u$) 1287 for an additional margin of error over missed upper true alarms. That is, an upper baseline ($B_u$) 1287 is generated that tracks a lower-than-average range of parameter values, effectively lowering the upper adaptive threshold $AT_u$ slightly below a threshold calculated based upon a true parameter average. In an embodiment, the under-bias calculator 1267 rejects an upper range of parameter values from each time segment 1252 of the sliding window 1250 so as to generate an under-biased time segment 1267.

Additionally shown in FIG. 12B, the trend calculator 1270 outputs an over-biased trend 1272 of the remaining higher range of parameter values in each over-biased segment 1262. Further, the trend calculator 1270 outputs an under-biased trend 1277 of the remaining lower range of parameter values in each under-biased segment 1267. In an embodiment, the biased trends 1272, 1277 are each an average of the values in the corresponding biased time segments 1262, 1267. In other embodiments, the biased trends 1272, 1277 are each a median or mode of the values in the corresponding biased time segments 1262, 1267. The response limiter 1280 advantageously limits the extent to which the baseline 1222 outputs track the biased trends 1272, 1277. Accordingly, the baseline 1222 outputs track only relatively longer-lived transitions of the parameter 1201, but do not track (and hence mask) physiologically significant parameter events. In an embodiment, the response limiter 1280 has a low pass transfer function. In an embodiment, the response limiter 1280 is a slew rate limiter.

Figure 13A:
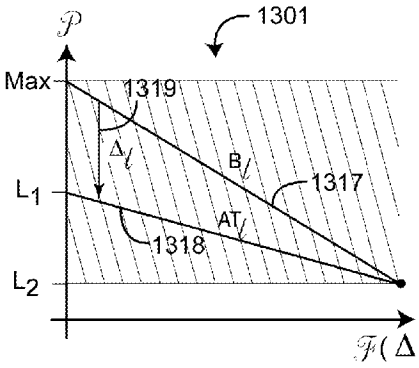
FIGS. 13A-E are physiological parameter versus delta space graphs illustrating a lower-limit adaptive threshold, an upper-limit adaptive threshold, and a combined lower- and upper-limit adaptive threshold in various delta spaces.

FIGS. 13A-E illustrate parameter (P) operating ranges and ideal ranges in view of both lower and upper parameter limits. As shown in FIG. 13A, as the baseline ($B_l$) 1317 decreases (increases) the adaptive threshold ($AT_l$) 1318 monotonically decreases (increases) between $L_1$ and $L_2$. Further, as the baseline ($B_l$) 1317 decreases (increases) the delta ($\Delta_l$) 1319 difference between the baseline ($B_l$) 1317 and the adaptive threshold ($AT_l$) 1318 monotonically decreases (increases) between Max−$L_1$ and 0.

Figure 13B:
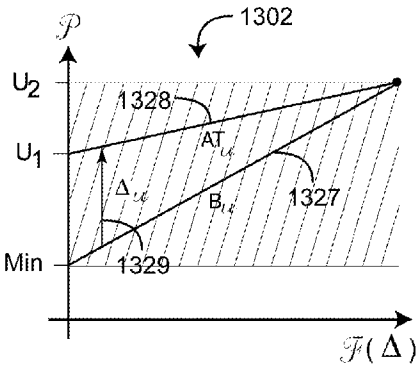

As shown in FIG. 13B, as the baseline ($B_u$) 1327 increases (decreases) the adaptive threshold ($AT_u$) 1328 monotonically increases (decreases) between $U_1$ and $U_2$. Further, as the baseline ($B_u$) 1327 increases (decreases) the delta ($\Delta_u$) 1329 difference between the adaptive threshold ($AT_u$) 1328 and the baseline ($B_u$) 1327 monotonically decreases (increases) between Min−$U_1$ and 0.

Figure 13C:
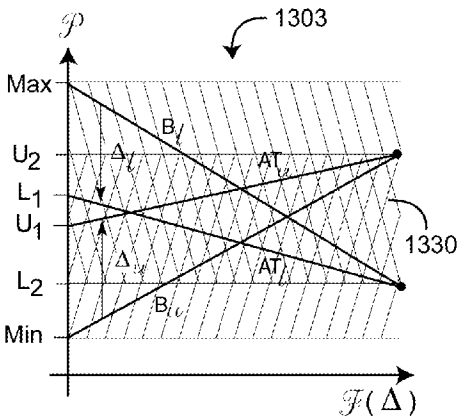

As shown in FIG. 13C, combining FIGS. 13A-B, the parameter (P) operating range is bounded by the overlapping regions of 13A and 13B 1330 having an upper bound of $U_2$ and a lower bound of $L_2$. In particular, $L_1$, $L_2$ are the upper and lower limits of the lower adaptive alarm threshold $AT_l$; and $U_2$, $U_1$ are the upper and lower limits of the upper adaptive alarm threshold $AT_u$.

Figure 13D:
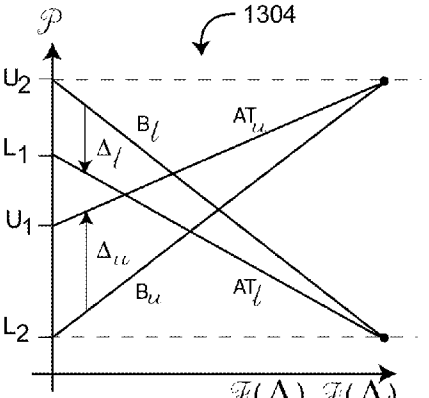
Figure 13E:
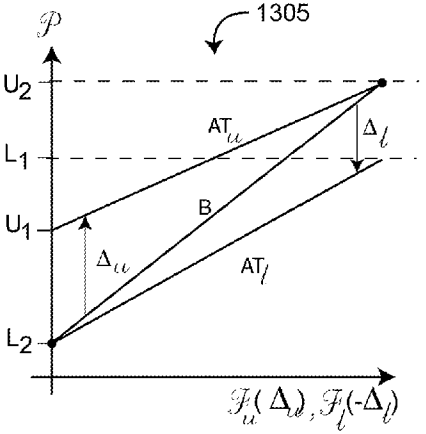

FIG. 13D illustrates parameter (P) versus the overlapping independent delta domains $F_u$, $F_l$ for upper and lower baselines $B_u$, $B_l$; adaptive thresholds $AT_u$, $AT_l$ and deltas $\Delta_u$, $\Delta_l$, based upon FIGS. 13A-C. FIG. 13E illustrates parameter (P) versus the overlapping independent delta domains $F_u$, $F_l$ (reversed); for upper and lower baselines $B_u$, $B_l$; adaptive thresholds $AT_u$, $AT_l$ and deltas $\Delta_u$, $\Delta_l$, As shown in FIG. 13E, the equations for bi-lateral adaptive thresholds are:

$$\Delta_u = -\left(\frac{U_1 - L_2}{U_2 - L_2}\right)(B - L_2) + (U_1 - L_2) \tag{9}$$

$$AT_u = B + \Delta_u \tag{10}$$

where $\Delta_u = U_1 -_2$ @ $B = L_2$; and $\Delta_u = 0$ @ $B = U_2$; and where $AT_u = U_1$ @ $B = L_2$; and $AT_u = U_2$ @ $B = U_2$.

Further:

$$\Delta_l = \left(\frac{U_2 - L_1}{U_2 - L_2}\right)(B - L_2) \quad (11)$$

$$AT_l = B - \Delta_l \quad (12)$$

where $\Delta_l = U_2 - L_1$ @ $B = U_2$; and $\Delta_l = 0$ @ $B = L_2$; and where $AT_l = L_1$ @ $B = U_2$; $AT_l = L_2$ @ $B = L_2$.

Although shown as a linear relationship, in general:

$$\Delta_l = f_1(B); \Delta_u = f_2(B)$$

That is, $\Delta_l$ and $\Delta_u$ can each be a linear function of B, a non-linear function of B or a piecewise linear function of B, to name a few, in a manner similar to that described with respect to FIGS. 5B and 10B, above.

Figure 14:
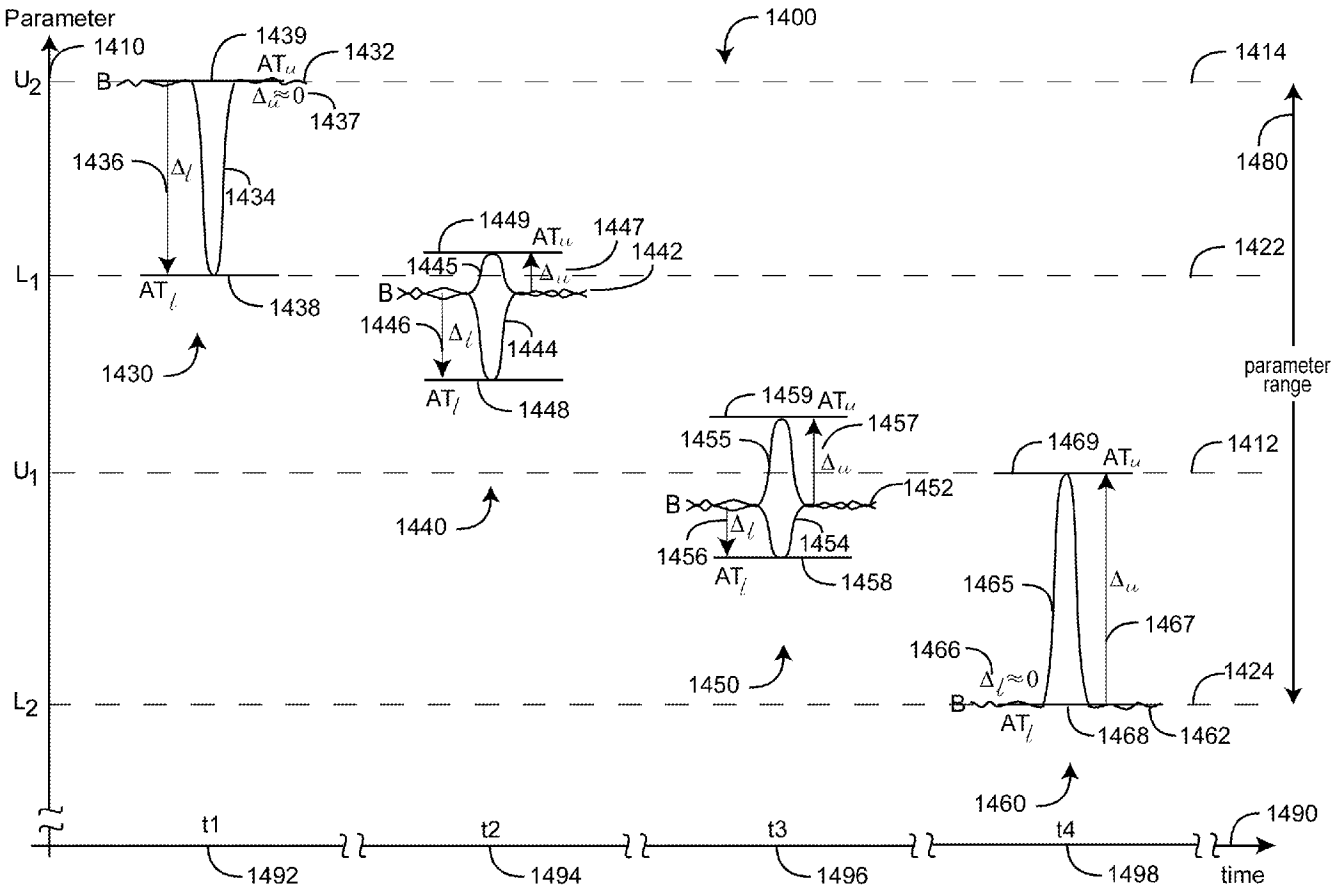
FIG. 14 is an exemplar graph of a physiological parameter versus time illustrating an adaptive alarm system having both lower and upper alarm limits.

FIGS. 14A-B illustrate the operational characteristics an adaptive alarm system 1200 (FIGS. 12A-B) having upper limits $U_1$, $U_2$ 1412, 1414 and lower limits $L_1$, $L_2$ 1422, 1424. An alarm 1212 (FIG. 12A) output is responsive to a baseline (B) 1432, 1442, 1452, 1462; an upper delta ($\Delta_u$) 1437, 1447, 1457, 1467; and a corresponding upper adaptive threshold ($AT_u$) 1439, 1449, 1459, 1469, according to EQS. 9-10, above. Further, the alarm 1212 (FIG. 12A) output is responsive to a lower delta ($\Delta_l$) 1436, 1446, 1456, 1466 and a corresponding lower adaptive threshold ($AT_l$) 1438, 1448, 1458, 1468, according to EQS. 11-12, above.

As shown in FIGS. 14A-B, a physiological parameter 1410 is graphed versus time 1490 for various time segments $t_1$, $t_2$, $t_3$, $t_4$ 1492-1498. The parameter range (PR) 1480 is:

$$PR = U_2 - L_2 \quad (13)$$

the lower adaptive threshold $AT_l$ range is:

$$ATR_l = L_1 - L_2 \quad (14)$$

the upper adaptive threshold $AT_U$ range is:

$$ATR_l = U_2 - U_1 \quad (15)$$

As shown in FIG. 14A, during a first time period $t_1$ 1492, a parameter segment 1430 has a baseline (B) 1432 at about $U_2$ 1414. As such, $\Delta_l$ 1436$=U_2-L_1$; $\Delta_u$ 1437$=0$; $AT_l$ 1438$=L_1$; $AT_u$ 1439$=U_2$. Accordingly, a negative transient 1434 having a size less than $U_2-L_1$ does not trigger an alarm.

Also shown in FIG. 14A, during a second time period $t_2$ 1494, a parameter segment 1440 has a baseline (B) 1442 less than $U_2$. As such, $\Delta_l$ 1446 is less than $U_1-L_1$ and the adaptive threshold ($AT_u$) 1447 is between $U_1$ and $U_2$. Accordingly, a smaller negative transient 1444 will trigger the alarm as compared to the negative transient 1434 in the first time segment 1430.

Further shown in FIG. 14A, during a third time period $t_3$ 1496, a parameter segment 1450 has a baseline (B) 1452 less than $U_1$ 1412. As such, a smaller negative transient 1454 will trigger the alarm as compared to the negative transient 1444 in the second time segment 1440. However, a larger positive transient 1455 is needed to trigger the alarm as compared to the positive transient 1445 in the second time segment 1440.

Additionally shown in FIG. 14A, during a fourth time period $t_4$ 1460, a parameter segment 1460 has a baseline (B) 1462 at about $L_2$ 1424. As such, $\Delta_l$ 1466$=0$; $\Delta_u$ 1467$=U_1-L_2$; $AT_l$ 1468$=L_2$; $AT_u$ 1469$=U_1$. Accordingly, a positive transient 1465 having a size less than $U_1-L_2$ does not trigger an alarm.

An adaptive alarm system has been disclosed in detail in connection with various embodiments. These embodiments are disclosed by way of examples only and are not to limit the scope of the claims that follow. One of ordinary skill in the art will appreciate many variations and modifications.

What is claimed is:

[1. A system for reducing electronic alarms in a medical patient monitoring system, the system comprising:

an optical sensor configured to transmit optical radiation into a tissue site of a patient and detect attenuated optical radiation indicative of at least one physiological parameter of a patient; and one or more hardware processors in electronic communication with the optical sensor, the one or more hardware processors configured to:

measure oxygen saturation values of a patient over a first period of time;

determine if at least one oxygen saturation value obtained over the first period of time exceeds a first alarm threshold;

determine whether a first alarm should be triggered based on the determination that the at least one oxygen saturation value obtained over the first period of time exceeds the first alarm threshold;

determine a second alarm threshold to be applied during a second period of time subsequent to the first period of time, the second alarm threshold replacing the first alarm threshold, the second alarm threshold being determined by:

comparing at least a first oxygen saturation value obtained during the first time period with a lower limit associated with oxygen saturation; and computing a second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes;

measure oxygen saturation values of a patient over the second period of time to determine at least a second oxygen saturation value; and determine whether a second alarm should be triggered by determining if at least one oxygen saturation value obtained during the second period of time exceeds the second alarm threshold and triggering an alarm if it is determined the second alarm should be triggered.]

[2. The system of claim 1, wherein the one or more hardware processors are configured to calculate a first baseline measurement from the measured oxygen saturation values over the first period of time and wherein the at least one oxygen saturation value obtained during the first period of time corresponds to the first baseline measurement.]

[3. The system of claim 2, wherein the one or more hardware processors are configured to calculate a second baseline measurement from the measured oxygen saturation values over the second period of time and wherein the at least one oxygen saturation value obtained during the second period of time corresponds to the second baseline measurement.]

[4. The system of claim 1, wherein the lower limit is predefined and corresponds to a minimum parameter value for oxygen saturation.]

[5. The system of claim 1, wherein the one or more hardware processors are further configured to wait for a time delay prior to the triggering of the second alarm, and wherein the time delay is a function of the second alarm threshold.]

[6. The system of claim 5, wherein the time delay decreases as the difference between the at least first oxygen saturation value and the lower limit diminishes.]

[7. The system of claim 1, wherein the first alarm threshold is predetermined.]

[8. A system for reducing electronic alarms in a medical patient monitoring system including a pulse oximeter in communication with an optical sensor, the system comprising one or more hardware processors configured to:

measure oxygen saturation values of a patient over a first period of time;

determine if at least one oxygen saturation value obtained over the first period of time exceeds a first alarm threshold;

determine whether a first alarm should be triggered based on the determination that the at least one oxygen saturation value obtained over the first period of time exceeds the first alarm threshold;

compare at least a first oxygen saturation value obtained during the first time period with a lower limit associated with oxygen saturation;

compute a second alarm threshold based on the comparison;

determine a time delay based on the computed second alarm threshold, wherein the time delay approaches zero as the first oxygen saturation value approaches the lower limit;

measure oxygen saturation values of a patient over the second period of time to determine at least a second oxygen saturation value; and determine whether a second alarm should be triggered by determining if at least one oxygen saturation value obtained during the second period of time exceeds the second alarm threshold for the time delay and triggering an alarm if it is determined the second alarm should be triggered.]

[9. The system of claim 8, wherein the first alarm threshold is predetermined.]

[10. The system of claim 8, wherein the lower limit is predefined and corresponds to a minimum parameter value for oxygen saturation.]

[11. The system of claim 8, where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes.]

[12. An electronic method for reducing electronic alarms in a medical patient monitoring system, the electronic method comprising:

measuring oxygen saturation values of a patient over a first period of time;

determining if at least one oxygen saturation value determined over the first period of time exceeds a first alarm threshold;

determining whether a first alarm should be triggered based on the determination that at least one oxygen saturation value obtained during the first period of time exceeds the first alarm threshold;

comparing at least a first oxygen saturation value obtained during the first time period with a lower limit associated with oxygen saturation;

computing the second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes and wherein the second alarm threshold is configured to be applied during a second period of time subsequent to the first period of time, the second alarm threshold replacing the first alarm threshold;

measuring oxygen saturation values of a patient over the second period of time to determine at least a second oxygen saturation value; and determining whether a second alarm should be triggered by determining if at least one oxygen saturation value obtained during the second period of time exceeds the second alarm threshold and triggering an alarm if it is determined the second alarm should be triggered.]

[13. The electronic method of claim 12, wherein the one or more hardware processors are configured to calculate a first baseline measurement from the measured oxygen saturation values over the first period of time and wherein the at least one oxygen saturation value obtained during the first period of time corresponds to the first baseline measurement.]

[14. The electronic method of claim 13, wherein the one or more hardware processors are configured to calculate a second baseline measurement from the measured oxygen saturation values over the second period of time and wherein the at least one oxygen saturation value obtained during the second period of time corresponds to the second baseline measurement.]

[15. The electronic method of claim 12, wherein the lower limit is predefined and corresponds to a minimum parameter value for oxygen saturation.]

[16. The electronic method of claim 12, wherein the one or more hardware processors are further configured to wait for a time delay prior to the triggering of the second alarm, and wherein the time delay is a function of the second alarm threshold.]

[17. The electronic method of claim 16, wherein the time delay decreases as the difference between the at least first oxygen saturation value and the lower limit diminishes.]

[18. The electronic method of claim 12, wherein the first alarm threshold is predetermined.]

*19. A non-transitory physical computer storage comprising computer-executable instructions stored thereon that, when executed by one or more processors, are configured to implement a process comprising:*

*transmitting optical radiation into a tissue site of a patient and detecting attenuated optical radiation indicative of an oxygen saturation of a patient;*

*defining a limit that corresponds to a reference level for a determination of an alarm threshold; and*

*using an alarm threshold in determining whether to activate an alarm, the alarm threshold being at a value less than a prior oxygen saturation of the patient by a difference, wherein the difference diminishes based on the prior oxygen saturation of the patient approaching the limit.*

*20. The non-transitory physical computer storage of claim 19, wherein the difference diminishes in response to a decrease in the patient's oxygen saturation until it reaches zero.*

*21. The non-transitory physical computer storage of claim 19, wherein the diminishment is proportional to the difference.*

*22. The non-transitory physical computer storage of claim 19, wherein the diminishment is a piecewise function of discrete diminishment steps.*

*23. The non-transitory physical computer storage of claim 19, wherein the process further comprises automatically determining the alarm threshold.*

*24. The non-transitory physical computer storage of claim 19, wherein the limit is set at 85% oxygen saturation.*

*25. The non-transitory physical computer storage of claim 19, wherein the limit is set at 80% oxygen saturation.*

*26. The non-transitory physical computer storage of claim 19, wherein the limit is set between 80% to 85% oxygen saturation.*

*27. The non-transitory physical computer storage of claim 19, wherein the limit is predefined.*

*28. The non-transitory physical computer storage of claim 19, wherein the process further comprises waiting for a time delay prior to activating the alarm, wherein the time delay is based on the alarm threshold.*

*29. The non-transitory physical computer storage of claim 28, wherein the time delay decreases based on the prior oxygen saturation of the patient approaching the limit.*

* * * * *